(12) United States Patent
Vasmatzis et al.

(10) Patent No.: US 9,677,137 B2
(45) Date of Patent: Jun. 13, 2017

(54) TBL1XR1 AND TP63 TRANSLOCATIONS

(71) Applicant: Mayo Foundation for Medical Education and Research, Rochester, MN (US)

(72) Inventors: George Vasmatzis, Oronoco, MN (US); Andrew L. Feldman, Rochester, MN (US); Sarah H. Johnson, Rochester, MN (US); Rhett P. Ketterling, Rochester, MN (US); Ryan A. Knudson, Byron, MN (US); Kathryn E. Pearce, Rochester, MN (US); Julie C. Porcher, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 103 days.

(21) Appl. No.: 14/380,995

(22) PCT Filed: Feb. 27, 2013

(86) PCT No.: PCT/US2013/028056
§ 371 (c)(1),
(2) Date: Aug. 26, 2014

(87) PCT Pub. No.: WO2013/130634
PCT Pub. Date: Sep. 6, 2013

(65) Prior Publication Data
US 2015/0037796 A1 Feb. 5, 2015

Related U.S. Application Data

(60) Provisional application No. 61/603,759, filed on Feb. 27, 2012.

(51) Int. Cl.
C07H 21/02 (2006.01)
C07H 21/04 (2006.01)
C12Q 1/68 (2006.01)

(52) U.S. Cl.
CPC ........ *C12Q 1/6883* (2013.01); *C12Q 1/6886* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| 4,683,202 | A | 7/1987 | Mullis | |
| 6,399,364 | B1 * | 6/2002 | Reeve | C12Q 1/6874 435/287.1 |
| 2002/0192692 | A1 * | 12/2002 | Palanisamy | C12Q 1/6841 435/6.14 |
| 2003/0068625 | A1 | 4/2003 | Sheehan et al. | |
| 2003/0134279 | A1 | 7/2003 | Isola et al. | |
| 2011/0039735 | A1 | 2/2011 | Yamada et al. | |

OTHER PUBLICATIONS

Vasmatzis et al Blood. published online Aug. 1, 2012. 120(11): 2280-2289 and supplemental materials, pp. 1-28.*
Scott et al Blood. published online Apr. 11, 2012. 119(21):4949-4952 and supplemental tables, pp. 1-3.*
Osoegawa et al Genome Research. Cold Spring Harbor Laboratory Press. 2001 11: 483-496.*
Morrison (Molecular Cytogenetics. Protocols and Applications (Fan, Y.-S., ed) 2003., pp. 21-40.*
Deaven et al. 1986. Cold Spring Harbor Symposia Quantitative Biology. vol. L1, p. 159-167.*
NCBI Database Clone Summary for CTD-2316F21, available via url: <ncbi.nlm.nih.gov/clone/25907/>, printed on Aug. 8, 2016.*
Abouyabis et al., "Incidence and outcomes of the peripheral T-cell lymphoma subtypes in the United States," *Leuk Lymphoma.*, 49(11):2099-2107, Nov. 2008.
Bateman et al., "Acquisition of genome-wide copy number alterations in monozygotic twins with acute lymphoblastic leukemia," *Blood*, 115(17):3553-3558, Epub Jan. 8, 2010.
Braggio et al., "Primary central nervous system lymphomas: a validation study of array-based comparative genomic hybridization in formalin-fixed paraffin-embedded tumor specimens," *Clin Cancer Res.*, 17(13):4245-4253, Epub May 11, 2011.
Cha-aim et al., "Reliable fusion PCR mediated by GC-rich overlap sequences," *Gene.*, 434(1-2):43-49, Epub Dec. 29, 2008.
Cheung et al., "High resolution analysis of follicular lymphoma genomes reveals somatic recurrent sites of copy-neutral loss of heterozygosity and copy number alterations that target single genes," *Genes Chromosomes Cancer*, 49(8):669-681, Aug. 2010.
Cui et al., "NPM-ALK inhibits the p53 tumor suppressor pathway in an MDM2 and JNK-dependent manner," *Blood*, 113(21):5217-5227, Epub Mar. 13, 2009.
DeYoung et al., "Tumor-specific p73 up-regulation mediates p63 dependence in squamous cell carcinoma," *Cancer Res.*, 66(19):9362-9368, Oct. 1, 2006.
Drakos et al., "The therapeutic potential of p53 reactivation by nutlin-3a in ALK+ anaplastic large cell lymphoma with wild-type or mutated p53," *Leukemia*, 23(12):2290-2299, Epub Sep. 10, 2009.
Druker, "Translation of the Philadelphia chromosome into therapy for CML," *Blood*, 112(13):4808-4817, Dec. 15, 2008.
Feldman et al., "Discovery of recurrent t(6;7)(p25.3;q32.3) translocations in Alk-negative anaplastic large cell lymphomas by massively parallel genomic sequencing," *Blood*, 117(3):915-919, Epub Oct. 28, 2010.

(Continued)

*Primary Examiner* — Carla Myers
(74) *Attorney, Agent, or Firm* — Fish & Richardson P.C.

(57) ABSTRACT

This document provides methods and materials involved in detecting translocations of TBL1XR1 and TP63 nucleic acid. For example, methods and materials for detecting TBL1XR1 and TP63 gene rearrangements (e.g., translocations) associated with cancer (e.g., T-cell lymphomas) as well as methods and materials for detecting cancers (e.g., T-cell lymphomas) with a dominant negative TP63 phenotype are provided.

5 Claims, 21 Drawing Sheets

(56) References Cited

OTHER PUBLICATIONS

Feldman et al., "Incidence of TCR and TCL1 gene translocations and isochromosome 7q in peripheral T-cell lymphomas using fluorescence in situ hybridization," *Am J Clin Pathol.*, 130(2):178-185, Aug. 2008.

Feldman et al., "Recurrent translocations involving the IRF4 oncogene locus in peripheral T-cell lymphomas," *Leukemia*, 23(3):574-580, Epub Nov. 6, 2008.

Fomenkov et al., "RACK1 and stratifin target DeltaNp63alpha for a proteasome degradation in head and neck squamous cell carcinoma cells upon DNA damage," *Cell Cycle*, 3(10):1285-1295, Epub Oct. 6, 2004.

Gascoyne et al., "Prognostic significance of anaplastic lymphoma kinase (ALK) protein expression in adults with anaplastic large cell lymphoma," *Blood*, 93(11):3913-3921, Jun. 1, 1999.

GenBank Accession No. NM_000332.3 GI:189491746 "*Homo sapiens* ataxin 1 (ATXN1), transcript variant 1, mRNA," Dec. 18, 2011, 7 pages.

GenBank Accession No. NM_001114978 "*Homo sapiens* tumor protein p63 (TP63), transcript variant 2, mRNA," Jan. 22, 2012, 6 pages.

GenBank Accession No. NM_001114979 "*Homo sapiens* tumor protein p63 (TP63), transcript variant 3, mRNA," Jan. 22, 2012, 5 pages.

GenBank Accession No. NM_001114980 "*Homo sapiens* tumor protein p63 (TP63), transcript variant 4, mRNA" Jan. 22, 2012, 5 pages.

GenBank Accession No. NM_001114981 "*Homo sapiens* tumor protein p63 (TP63), transcript variant 5, mRNA" Jan. 22, 2012, 5 pages.

GenBank Accession No. NM_001114982 "*Homo sapiens* tumor protein p63 (TP63), transcript variant 6, mRNA" Jan. 22, 2012, 5 pages.

GenBank Accession No. NM_003722 "*Homo sapiens* tumor protein p63 (TP63), mRNA," Feb. 17, 2008, 5 pages.

GenBank Accession No. NM_003722.4 "*Homo sapiens* tumor protein p63 (TP63), transcript variant 1, mRNA," Jan. 22, 2012, 6 pages.

GenBank Accession No. NM_004514.3 "*Homo sapiens* forkhead box K2 (FOXK2), mRNA," Aug. 13, 2011, 6 pages.

GenBank Accession No. NM_024665 "*Homo sapiens* transducin (beta)-like 1X-linked receptor 1 (TBL1XR1), mRNA," Jan. 13, 2008, 5 pages.

GenBank Accession No. NM_024665 (GI No. 79718) "*Homo sapiens* transducin (beta)-like 1 X-linked receptor 1 (TBL1XR1), mRNA," Jan. 29, 2012, 7 pages.

Hahn et al., "Finding fusion genes resulting from chromosome rearrangement by analyzing the expressed sequence databases," *Proc Natl Acad Sci U S A.*, 101(36):13257-13261, Epub Aug. 23, 2004.

Hastak et al., "Synergistic chemosensitivity of triple-negative breast cancer cell lines to poly(ADP-Ribose) polymerase inhibition, gemcitabine, and cisplatin," *Cancer Res.*, 70(20):7970-7980, Epub Aug. 26, 2010.

Jaffe, "Anaplastic large cell lymphoma: the shifting sands of diagnostic hematopathology," *Mod Pathol.*, 14(3):219-228, Mar. 2001.

James et al., "RGS17, an overexpressed gene in human lung and prostate cancer, induces tumor cell proliferation through the cyclic AMP-PKA-CREB pathway," *Cancer Res.*, 69(5):2108-2116, Epub Feb. 24, 2009.

Jardin et al., "Diffuse large B-cell lymphomas with CDKN2A deletion have a distinct gene expression signature and a poor prognosis under R-CHOP treatment: a GELA study," *Blood*, 116(7):1092-1104, Epub Apr. 30, 2010.

Kaneko et al., "A novel translocation, t(2;5)(p23;q35), in childhood phagocytic large T-cell lymphoma mimicking malignant histiocytosis," *Blood*, 73(3):806-813, Feb. 15, 1989.

Lazzari et al., "HIPK2 phosphorylates ΔNp63α and promotes its degradation in response to DNA damage," *Oncogene*, 30(48):4802-4813, Epub May 23, 2011.

Leong et al., "The p63/p73 network mediates chemosensitivity to cisplatin in a biologically defined subset of primary breast cancers," *J Clin Invest.*, 117(5):1370-1380, Epub Apr. 19, 2007.

Li and Morris, "Development of anaplastic lymphoma kinase (ALK) small-molecule inhibitors for cancer therapy," *Med Res Rev.*, 28(3):372-412, May 2008.

Li et al., "WW domain-containing E3 ubiquitin protein ligase 1 targets p63 transcription factor for ubiquitin-mediated proteasomal degradation and regulates apoptosis," *Cell Death Differ.*, 15(12):1941-1951, Epub Sep. 19, 2008.

Martinez-Delgado et al., "Correlation between mutations in p53 gene and protein expression in human lymphomas," *Am J Hematol.*, 55(1):1-8, May 1997.

Matsushima et al., "Post-thymic T cell lymphomas frequently overexpress p53 protein but infrequently exhibit p53 gene mutations," *Am J Pathol.*, 144(3):573-584, Mar. 1994.

Parker et al., "The complex genomic profile of ETV6-RUNX1 positive acute lymphoblastic leukemia highlights a recurrent deletion of TBL1XR1," *Genes Chromosomes Cancer.*, 47(12):1118-1125, Dec. 2008.

Patnaik et al., "Chromosome 9p24 abnormalities: prevalence, description of novel JAK2 translocations, JAK2V617F mutation analysis and clinicopathologic correlates," *Eur J Haematol.*, 84(6):518-524, Epub Mar. 11, 2010.

Pescarmona et al., "p53 over-expression identifies a subset of nodal peripheral T-cell lymphomas with a distinctive biological profile and poor clinical outcome," *J Pathol.*, 195(3):361-366, Oct. 2001.

Petit et al., "Expression of p53 protein in T- and natural killer-cell lymphomas is associated with some clinicopathologic entities but rarely related to p53 mutations," *Hum Pathol.*, 32(2):196-204, Feb. 2001.

Rassidakis et al., "p53 gene mutations are uncommon but p53 is commonly expressed in anaplastic large-cell lymphoma," *Leukemia.*, 19(9):1663-1669, Sep. 2005.

Rocca et al., "Pathologic complete remission rate after cisplatin-based primary chemotherapy in breast cancer: correlation with p63 expression," *Cancer Chemother Pharmacol.*, 61(6):965-971, Epub Jul. 18, 2007.

Rocco et al., "p63 mediates survival in squamous cell carcinoma by suppression of p73-dependent apoptosis," *Cancer Cell.*, 9(1):45-56, Jan. 2006.

Savage et al., "ALK—anaplastic large-cell lymphoma is clinically and immunophenotypically different from both ALK+ ALCL and peripheral T-cell lymphoma, not otherwise specified: report from the International Peripheral T-Cell Lymphoma Project," *Blood*, 111(12):5496-5504, Epub Apr. 2, 2008.

Savage et al., "Characterization of peripheral T-cell lymphomas in a single North American institution by the WHO classification," *Ann Oncol.*, 15(10):1467-1475, Oct. 2004.

The Non-Hodgkin's Lymphoma Classification Project, "A clinical evaluation of the International Lymphoma Study Group classification of non-Hodgkin's lymphoma. The Non-Hodgkin's Lymphoma Classification Project," *Blood*, 89(11):3909-3918, Jun. 1, 1997.

Turturro et al., "Comparison of the effects of recombinant adenovirus-mediated expression of wild-type p53 and p27Kip1 on cell cycle and apoptosis in SUDHL-1 cells derived from anaplastic large cell lymphoma," *Leukemia*, 15(8):1225-1231, Aug. 2001.

Vilgelm et al., "Therapeutic prospects for p73 and p63: rising from the shadow of p53," *Drug Resist Updat.*, 11(4-5):152-163, Epub Sep. 17, 2008.

Wada et al., "IRF4 Translocations are Specific for Cutaneous Anaplastic Large Cell Lymphoma in Skin Biopsies involved by T-cell Lymphoproliferative Disorders," *Mod Pathol.*, 22 suppl 1:289A Abstract 1308, 2009.

Wada et al., "Specificity of IRF4 translocations for primary cutaneous anaplastic large cell lymphoma: a multicenter study of 204 skin biopsies," *Mod Pathol.*, 24(4):596-605, Epub Dec. 17, 2010.

Wilson et al., "Novel disease targets and management approaches for diffuse large B-cell lymphoma," *Leuk Lymphoma*, 51 Suppl 1:1-10, Aug. 2010.

Yang and McKeon, "P63 and P73: P53 mimics, menaces and more," *Nat Rev Mol Cell Biol.*, 1(3):199-207, Dec. 2000.

(56) References Cited

OTHER PUBLICATIONS

Yang et al., "p63, a p53 homolog at 3q27-29, encodes multiple products with transactivating, death-inducing, and dominant-negative activities," *Mol Cell.*, 2(3):305-316, Sep. 1998.

Yoon et al., "Purification and functional characterization of the human N-CoR complex: the roles of HDAC3, TBL1 and TBLR1," *EMBO J.*, 22(6):1336-1346, Mar. 17, 2003.

Zangen et al., "DeltaNp63alpha levels correlate with clinical tumor response to cisplatin," *Cell Cycle.*, 4(10):1313-1315, Epub Oct. 1, 2005.

Zhang et al., "Key pathways are frequently mutated in high-risk childhood acute lymphoblastic leukemia: a report from the Children's Oncology Group," *Blood*, 118(11):3080-3087, Epub Jun. 16, 2011.

Zhang et al., "TBLR1 regulates the expression of nuclear hormone receptor co-repressors," *BMC Cell Biol.*, 7:31, Aug. 7, 2006.

International Search Report and Written Opinion for PCT/US2013/028056 mailed Jun. 6, 2013, 6 pages.

International Preliminary Report on Patentability for PCT/US2013/028056 mailed Sep. 12, 2014, 6 pages.

\* cited by examiner (SEQ ID NO: 6) TBL1XR1: ACATCTCTAGATTGGAATGTGAGTATCACTATATCC
                      ||||||||||||||||||||
(SEQ ID NO: 7) Fusion:  ACATCTCTAGATTGGAATCCACAGTACACGAACCTG
                                          ||||||||||||||||||||
(SEQ ID NO: 8) TP63:    TTCTGGGTGTCCTTGCAGCCACAGTACACGAACCTG
FIG. 1D
FIG. 1E
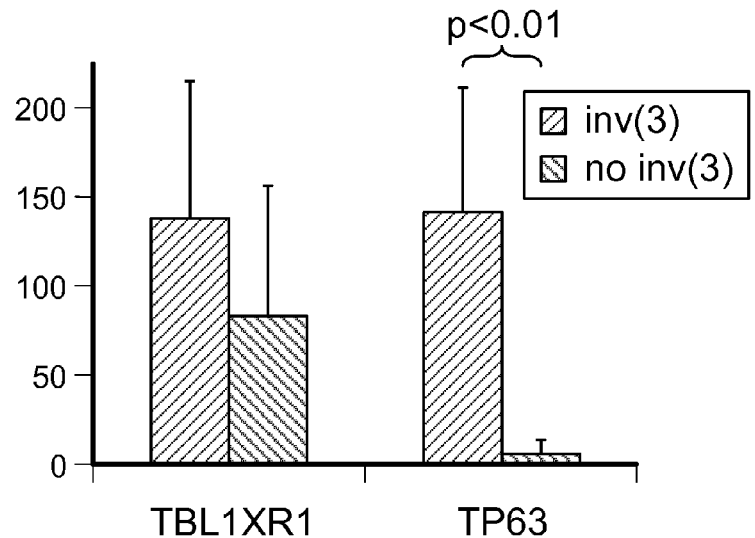
FIG. 1F
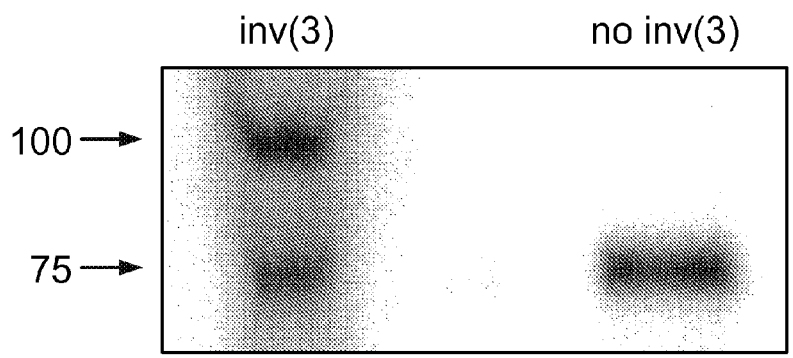
FIG. 1G

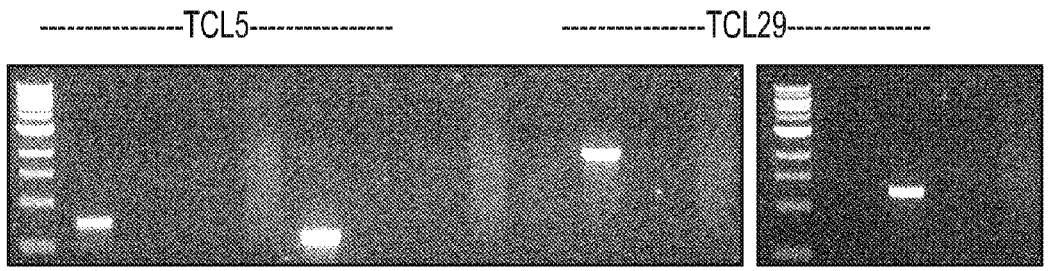

Rxn 196:
CNNNNNNNNNCNNANNNTTCTCNNGNCTCNNCAAGTAAGAATGAAGGTAGAGTGGTGGACT
GGGAAGAACATCAAATTCATAGTCTTACAATGATTTATTAGAAGTAAAAAAGAAAAACTTTA
AAATATGATTAGAAGGTTTTATATGGCCATTCCTCTAAATCCTTTACTGTCTAAAACGAAGTG
TGTGTGTATGATCCAAACAATATCATTGTTTCGAATGATCAGATTCTTAAATACTTGAATGTT
CCTTTCTATTATTAATCCCTTCCCACTATGAAATATTTGCCAATAAAAAGATCAACAAGGAAA
AGAGCCAGAAAAGAGCACAGGCTGACTTTATAGTTAATGAAGTAAGTACAACTGCCTACTTT
ACCAGGAGGAAAAGTCCATATAAATTTCTCTCAACTTATATTAAACGCTTATCTATTTGAATA
TTTCTTTTCTCTATTTTATTGTACCCAGTTTATACTAATATTTTTGCTTGTGAATAGGTAATAA
AAATGATTACTGCACGTGATGCATCTATGTAAATGATTAGTGGAATAAGTATTAAAGCATAA
GATATCAATTGGCTTTTGTTTTAAAAATACATTTACATAAATACGTACCAACATTCATGTAGA
ATCTGGCCTTGGTACGAAGATTTACTGGAGATGAAATGCACCCTGATGCTTATCATCTGATT
CATTAAAATACTCTCTTTACTGCTGAGTATTTGTAATTCAGTTAGATTTATTTCTTGACATCA
TCCTACACCCCCACCCCCGCACTCACGGACCCAATTTGCTCTATTTTGCTTGAAAGGTTGTAA
GTGGCCAAGATAACTATNAGTGAAAATTGTGATTTCTTCTAAAATTTAGAAGACACAAAGTT
TAGAAGAGAATTGGAAGCCACAAGAGATTAGAACATACATTTCAGAAACANGTTTGCANTAC
GTTCACGACTTCGGATTTGCCTCCCTTTACTTGTACTTTTGCATCCATAAATTTATGCACTTA
AAGGATGACGTGGTCATTGGCTGATATATAAGACCCATANGTTTAC (SEQ ID NO: 9)

Dark shading represents nucleotides aligning to TP63 on minus strand
Light shading represents nucleotides aligning to TBL1XR1 on plus strand

FIG. 2

TTCTCTTCTGTACCTGCGATTTAAACATGAAATACTAGAAAGTGCTTTGAGTACCTTAACCAT
AAAAAGTGCAGAATCTAAATTCTGTCTACCATTTTATCTTTTACTTGAACATGTATACAAATA
AAAAATTAAATCTAGAATACAACTGTAAGATTTACCACAGAACTCGTCTCCCTTTCTATGCCT
ATGAGACTTACCCATTTTTCAGAACTTAGCTGGTCACCCTAAAATGGGTGAGATCTAATATC
TTGCTTTGGAACTTAGCCTCAGACTAAAAATTGATTTGTTGAACTAATTCAGTGGCCTTCAGT
AGCTTCCTCAAATGCTAATTCTTATCACCTATCTGAGGCAGGAGAGGAAGGTAAACACTTAA
TTCATGCAATATTAGAACTTTAAAAGTTACTCAGTGTGTTCTGTTGATCATCCTTCAACTTAA
TGGTAGCTGATACCAAAAAGATCTCA (SEQ ID NO: 10)

Dark shading represents nucleotides aligning to TBL1XR1 on minus strand
Light shading represents nucleotides aligning to TP63 on plus strand

FIG. 2 (Cont.)

| Primer Name | Sequence (5' - 3') |
|---|---|
| inv3par-F | AGAAGGAGGGCAAGATGTTC (SEQ ID NO: 3) |
| inv3par-R | TTCTGAATCTGCTGGTCCAT (SEQ ID NO: 4) |

AGAAGGAGGGCAAGATGTTCCAA
GCAACAAGGATGTCACATCTCTA
GATTGGAATCCACAGTACACGAA
CCTGGGGCTCCTGAACAGCATGG
ACCAGCAGATTCAGAA (SEQ ID NO: 11)

TBL1XR1 AND TP63 TRANSLOCATIONS

CROSS-REFERENCE TO RELATED APPLICATIONS

This application is a National Stage application under 35 U.S.C. § 371 of International Application No. PCT/US2013/028056, having an International Filing Date of Feb. 27, 2013, which claims the benefit of U.S. Provisional Application Ser. No. 61/603,759, filed Feb. 27, 2012. The disclosure of the prior application is considered part of (and is incorporated by reference in) the disclosure of this application.

BACKGROUND

1. Technical Field

This document relates to methods and materials involved in detecting translocations of TBL1XR1 and TP63 nucleic acid. For example, this document provides methods and materials for detecting TBL1XR1 and TP63 gene rearrangements (e.g., translocations) associated with cancer (e.g., T-cell lymphomas) as well as methods and materials for detecting cancers with a dominant negative TP63 phenotype.

2. Background Information

T-cell lymphomas are fatal and have limited treatment options. Non-Hodgkin lymphomas represent the fifth most common neoplasm in the United States for men and women, with about 66,000 projected new cases for 2009. About 12% are derived from mature ("peripheral") T lymphocytes. The incidence of T-cell non-Hodgkin lymphomas appears to be increasing, and people with T-cell non-Hodgkin lymphomas have a shorter survival than those with B-cell or Hodgkin lymphomas.

SUMMARY

This document provides methods and materials involved in detecting translocations of TBL1XR1 and TP63 nucleic acid. For example, this document provides methods and materials for detecting TBL1XR1 and TP63 gene rearrangements (e.g., translocations) associated with cancer (e.g., T-cell lymphomas) as well as methods and materials for detecting cancers (e.g., T-cell lymphomas) with a dominant negative TP63 phenotype. TBL1XR1 nucleic acid is widely expressed nucleic acid that encodes a co-repressor of nuclear hormone transcription factors (Yoon et al., *EMBO J.*, 22(6):1336-1346 (2003) and Zhang et al., *BMC Cell Biology*, 7:31 (2006)). TP63 nucleic acid splice variants that retain the N-terminal transactivation (TA) domain result in TAp63 polypeptides that share functions with p53 polypeptides, including apoptosis, cell cycle arrest, and cellular senescence (Vilgelm et al., *Drug Resistance Updates: Reviews and Commentaries in Antimicrobial and Anticancer Chemotherapy*, 11(4-5):152-163 (2008)). Splice variants lacking the TA domain encode ΔNp63 isoforms that are potent dominant-negative inhibitors of p53 (Vilgelm et al., *Drug Resistance Updates: Reviews and Commentaries in Antimicrobial and Anticancer Chemotherapy*, 11(4-5):152-163 (2008) and Yang et al., *Mol. Cell.*, 2(3):305-316 (1998)) either by sequestering p53 into non-functional complexes or by competing for binding to p53 transcriptional targets (Yang and McKeon, *Nature Reviews Molecular Cell Biology*, 1(3):199-207 (2000)).

As described herein, a neoplasm sample (e.g., a T-cell lymphoma sample) can be assessed for the presence or absence of a TBL1XR1 and TP63 gene rearrangement. In some cases, the presence of a TBL1XR1 and TP63 gene rearrangement can indicate that a patient with T-cell lymphoma has a poor prognosis. For example, the presence of a TBL1XR1 and TP63 gene rearrangement can indicate that a patient with T-cell lymphoma has a T-cell lymphoma that can be classified as a CD30-positive peripheral T-cell lymphoma, not otherwise specified (CD30-positive PTCL-NOS), which can have a poorer prognosis than CD30-negative PTCL-NOS, or an ALK-negative anaplastic large-cell lymphoma (ALK-negative ALCL), which can have a poorer prognosis than ALK-positive ALCL. ALK refers to the anaplastic lymphoma kinase gene. In some cases, the presence of a TBL1XR1 and TP63 gene rearrangement can indicate that a patient has cancer cells (e.g., T-cell lymphoma cells) that express a dominant-negative form of TP63, which can have the ability to inhibit activity of the p53, p63, or p73 tumor suppressor at both the mRNA and polypeptide levels. In some cases, the presence of a TBL1XR1 and TP63 gene rearrangement can be mutually exclusive with other known abnormalities responsible for p53 abnormalities such as ALK translocations, TP53 deletions, and TP53 mutations.

Having the ability to identify patients with cancer cells having a TBL1XR1 and TP63 gene rearrangement can allow clinicians to classify the patient as potentially having a poor prognosis. In some cases, having the ability to identify patients with cancer cells having a TBL1XR1 and TP63 gene rearrangement can allow clinicians to select treatment options designed to inhibit the effects of a dominant-negative form of TP63. For example, patients identified as having cancer cells (e.g., T-cell lymphoma cells) that express a dominant-negative form of TP63 can be treated with cis-platinum or PARP small molecule inhibitors to decrease the dominant-negative form of TP63 using techniques similar to those described elsewhere (Leong et al., *J. Clin. Invest.*, 117(5):1370-1380 (2007); Zangen et al., *Cell Cycle*, 4(10):1313-1315 (2005); Rocca et al., *Cancer Chemother. Pharmaco.*, 61(6):965-971 (2008); Hastak et al., *Cancer Res.*, 70(20):7970-7980 (2010)).

In general, one aspect of this document features a primer pair comprising, or consisting essentially of, first and second primers, wherein an amplification reaction comprising the first and second primers has the ability to amplify a nucleic acid having a TBL1XR1 sequence and a TP63 sequence. The TBL1XR1 sequence can be at least 10 nucleotides. The TBL1XR1 sequence can be at least 50 nucleotides. The TBL1XR1 sequence can be at least 100 nucleotides. The TP63 sequence can be at least 10 nucleotides. The TP63 sequence can be at least 50 nucleotides. The TP63 sequence can be at least 100 nucleotides. The first primer can be between 13 and 100 nucleotides in length. The first primer can be between 15 and 50 nucleotides in length. The second primer can be between 13 and 100 nucleotides in length. The second primer can be between 15 and 50 nucleotides in length.

In another aspect, this document features an isolated nucleic acid comprising, or consisting essentially of, a TBL1XR1 sequence and a TP63 sequence. The TBL1XR1 sequence can be at least 10 nucleotides. The TBL1XR1 sequence can be at least 50 nucleotides. The TBL1XR1 sequence can be at least 100 nucleotides. The TP63 sequence can be at least 10 nucleotides. The TP63 sequence can be at least 50 nucleotides. The TP63 sequence can be at least 100 nucleotides.

In another aspect, this document features a method for assessing a cancer cell for a dominant negative TP63 phenotype. The method comprises, or consists essentially of, detecting the presence of a TBL1XR1 and TP63 gene rearrangement in the genome of the cancer cell. The cell can be a T cell lymphoma cell. The TBL1XR1 and TP63 gene rearrangement can result in the expression of a polypeptide containing the DNA-binding and oligomerization domains of a p63 polypeptide and lacking a transactivation domain of a p63 polypeptide.

In another aspect, this document features a composition for performing break-apart fluorescence in situ hybridization, wherein the composition comprises, or consists essentially of, a first nucleic acid probe comprising a first fluorescence label and a second nucleic acid probe comprising a second fluorescence label, wherein the first nucleic acid probe comprises a sequence that is less than 400 Kb and is capable of hybridizing to human genomic nucleic acid lacking a translocation involving a TP63 sequence at a position upstream of a TP63 sequence, wherein the second nucleic acid probe comprises a sequence that is less than 400 Kb and is capable of hybridizing to the human genomic nucleic acid lacking a translocation involving a TP63 sequence at a position downstream of a TP63 sequence, wherein the positions of hybridization of the first nucleic acid probe and the second nucleic acid probe define as gap that is between 150 Kb and 600 Kb in the human genomic nucleic acid lacking a translocation involving a TP63 sequence, and wherein a fluorescence in situ hybridization reaction comprising the first and second probes has the ability to identify a nucleic acid having a translocation involving a TP63 sequence. The gap can be between about 250 Kb and 350 Kb. The gap can be about 300 Kb.

In another aspect, this document features a composition for performing dual-fusion fluorescence in situ hybridization. The composition comprises, or consists essentially of, a first nucleic acid probe comprising a first fluorescence label and a second nucleic acid probe comprising a second fluorescence label, wherein the first nucleic acid probe comprises a nucleic acid molecule having a nucleotide sequence of at least 10 Kb in length that is present in a bacterial artificial chromosome selected from the group consisting of RP11-1105J22, RP11-626C4, CTD-3077M16, CTD-2547G9, and CTD-2118M13, and wherein the second nucleic acid probe comprises a nucleic acid molecule having a nucleotide sequence of at least 10 Kb in length that is present in a bacterial artificial chromosome selected from the group consisting of RP11-1148M8, RP11-1012L11, CTD-2316F21, and RP11-994L2. The first nucleic acid probe can comprise a nucleic acid molecule having a nucleotide sequence of at least 20 Kb in length that is present in a bacterial artificial chromosome selected from the group consisting of RP11-1105J22, RP11-626C4, CTD-3077M16, CTD-2547G9, and CTD-2118M13. The first nucleic acid probe can comprise a nucleic acid molecule having a nucleotide sequence of at least 50 Kb in length that is present in a bacterial artificial chromosome selected from the group consisting of RP11-1105J22, RP11-626C4, CTD-3077M16, CTD-2547G9, and CTD-2118M13. The second nucleic acid probe can comprise a nucleic acid molecule having a nucleotide sequence of at least 20 Kb in length that is present in a bacterial artificial chromosome selected from the group consisting of RP11-1148M8, RP11-1012L11, CTD-2316F21, and RP11-994L2. The second nucleic acid probe can comprise a nucleic acid molecule having a nucleotide sequence of at least 50 Kb in length that is present in a bacterial artificial chromosome selected from the group consisting of RP11-1148M8, RP11-1012L11, CTD-2316F21, and RP11-994L2.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1D is Sanger sequencing results revealing in-frame fusion with an identical breakpoint in all the cases studied to date. FIG. 1E is a schematic diagram identifying the location of the TP63 breakpoint (arrow) at the junction of the transactivation (TA) domain and DNA binding domain (DBD). The resultant transcript lacks TA, but contains DBD and oligomerization domain (OD), characteristic of a dominant-negative ΔNp63. FIG. 1F is a graph plotting TBL1XR1 expression in PTCLs. Cases with inv(3) exhibited expression of TP63 that was 28 times higher than in cases without inv(3) using real-time PCR. FIG. 1G is a photograph of a Western blot for p63 showing wild-type p63 (about 75 kD) in both a PTCL with inv(3) and a p63-positive cell line without inv(3). Additionally, the PTCL exhibited a band at about 100 kD, consistent with the predicted MW of the TBL1XR1-ΔNp63 fusion protein.

FIG. 2 contains a photograph of PCR results and genomic DNA sequence data for two cases, TCL5 and TCL29, with inv(3) as detected by next generation sequencing. The PCR results reveal the presence of bands confirming the two breakpoints in each case. Representative results of Sanger sequencing are shown.

FIG. 5A is a photograph of FISH results showing a PTCL with an IRF4 translocation showing abnormal separation of the red and green signals flanking the IRF4 gene (arrows). FIG. 5B is a graph of TP53 deletions that were assessed using mate-pair NGS. The case shown has a hemizygous TP53 deletion. The green bar represents aberrant sequences juxtaposing the two borders of the deleted region. Exons 4-10 of TP53 including exon/intron splice sites were sequenced using Sanger sequencing (not shown). FIG. 5C is a graph indicating that cases with inv(3) lacked other abnormalities.

DETAILED DESCRIPTION

Figure 1A:
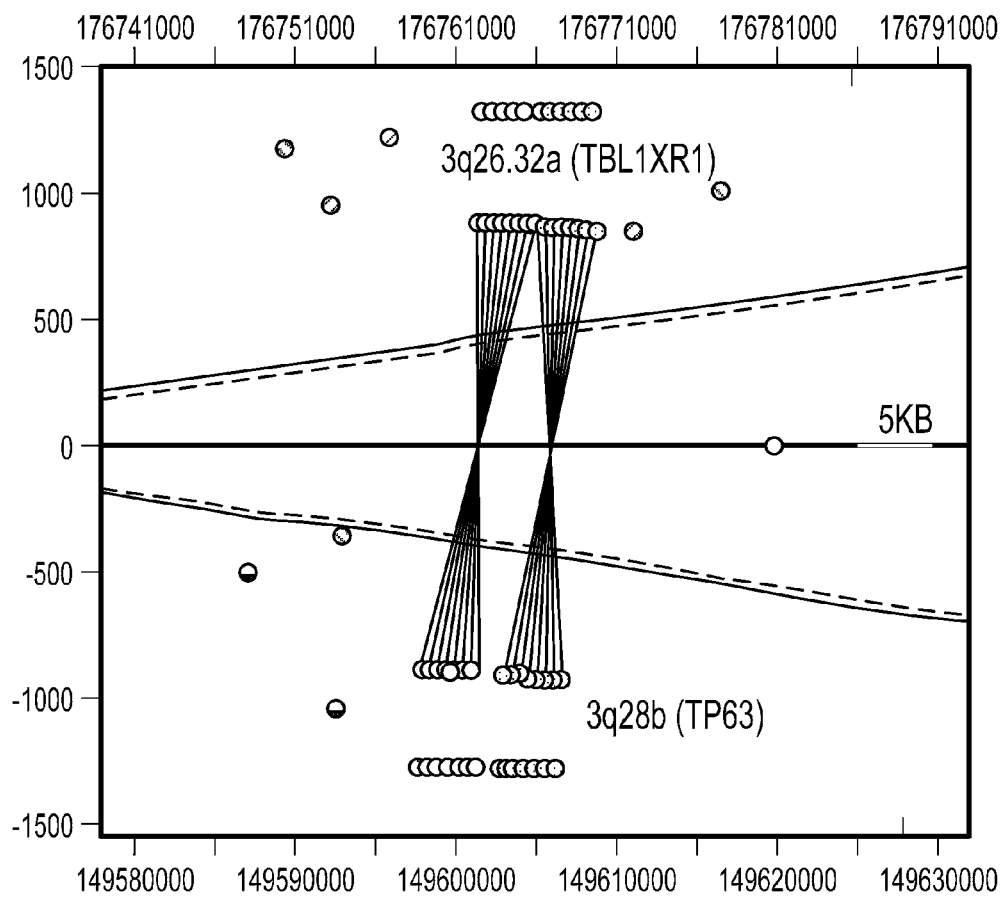
FIG. 1A is a graph plotting inv(3)(q26q28) involving TBL1XR1 and TP63 as discovered by genome-wide mate-pair next generation sequencing in 2/14 (14%) PTCLs. The figure shows the abnormal mate pairs (horizontal lines) in a case of PTCL, where each pair maps to TBL1XR1 at one end and to TP63 at the other end. Additional cases also were identified.

This document provides methods and materials involved in detecting translocations of TBL1XR1 and TP63 nucleic acid. For example, this document provides methods and materials for detecting TBL1XR1 and TP63 gene rearrangements (e.g., translocations) associated with cancer (e.g., T-cell lymphomas) as well as methods and materials for detecting cancers (e.g., T-cell lymphomas) with a dominant negative TP63 phenotype. In some cases, the methods and materials provided herein can be used to detect the presence of a TBL1XR1 and TP63 gene rearrangement within a cancer cell (e.g., a T-cell lymphoma cell), thereby indicating that the patient is likely to experience a poor prognosis. In some cases, the methods and materials provided herein can be used to detect the presence of a TBL1XR1 and TP63 gene rearrangement within a cancer cell (e.g., a T-cell lymphoma cell), thereby indicating that the patient has cancer cells (e.g., T-cell lymphoma cells) that express a dominant-negative form of TP63 and thereby indicating that the patient can be treated with treatment regimen designed to prevent the dominant-negative form of TP63 from inhibiting p53 activity and/or to increase p53 activity. Detecting a TBL1XR1 and TP63 gene rearrangement can be used to diagnose cancers (e.g., T-cell lymphomas) with a dominant negative TP63 phenotype, typically when known clinical symptoms of or known risk factors for cancer also are present.

A human TBL1XR1 nucleic acid can have the sequence set forth in GenBank Accession No. NM_024665 (GI No. 79718). A human TP63 nucleic acid can have the sequence set forth in GenBank Accession Nos. NM_003722.4, NM_001114982, NM_001114981, NM_001114980, NM_001114979, and NM_001114978 (GI No. 8626).

The term "nucleic acid" as used herein can be RNA or DNA, including cDNA, genomic DNA, and synthetic (e.g. chemically synthesized) DNA. The nucleic acid can be double-stranded or single-stranded. Where single-stranded, the nucleic acid can be the sense strand or the antisense strand. In addition, nucleic acid can be circular or linear.

The term "isolated" as used herein with reference to nucleic acid refers to a naturally-occurring nucleic acid that is not immediately contiguous with both of the sequences with which it is immediately contiguous (one on the 5' end and one on the 3' end) in the naturally-occurring genome of the organism or cell from which it is derived. For example, an isolated nucleic acid can be, without limitation, a recombinant DNA molecule of any length, provided one of the nucleic acid sequences normally found immediately flanking that recombinant DNA molecule in a naturally-occurring genome is removed or absent. Thus, an isolated nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include a recombinant DNA molecule that is part of a hybrid or fusion nucleic acid sequence.

The term "isolated" as used herein with reference to nucleic acid also includes any non-naturally-occurring nucleic acid since non-naturally-occurring nucleic acid sequences are not found in nature and do not have immediately contiguous sequences in a naturally-occurring genome. For example, non-naturally-occurring nucleic acid such as an engineered nucleic acid is considered to be isolated nucleic acid. Engineered nucleic acid can be made using common molecular cloning or chemical nucleic acid synthesis techniques. Isolated non-naturally-occurring nucleic acid can be independent of other sequences, or incorporated into a vector, an autonomously replicating plasmid, a virus (e.g., a retrovirus, adenovirus, or herpes virus), or the genomic DNA of a prokaryote or eukaryote. In addition, a non-naturally-occurring nucleic acid can include a nucleic acid molecule that is part of a hybrid or fusion nucleic acid sequence.

It will be apparent to those of skill in the art that a nucleic acid existing among hundreds to millions of other nucleic acid molecules within, for example, cDNA or genomic libraries, or gel slices containing a genomic DNA restriction digest is not to be considered an isolated nucleic acid.

In one embodiment, this document provides a primer pair having the ability to amplify a nucleic acid that includes (a) a TBL1XR1 nucleic acid sequence and (b) a TP63 nucleic acid sequence. For example, this document provides primer pairs that have the ability to amplify a nucleic acid that includes a TBL1XR1 nucleic acid sequence and a TP63 nucleic acid sequence as shown in FIG. 1D. The primers of the primer pair can be any appropriate length including, without limitation, lengths ranging from about 10 nucleotides to about 100 nucleotides (e.g., from about 15 nucleotides to about 100 nucleotides, from about 20 nucleotides to about 100 nucleotides, from about 15 nucleotides to about 75 nucleotides, from about 15 nucleotides to about 50 nucleotides, from about 15 nucleotides to about 25 nucleotides, from about 13 nucleotides to about 50 nucleotides, or from about 17 nucleotides to about 50 nucleotides).

The primers can be designed to amplify any appropriate length of the TBL1XR1 sequence and the TP63 sequence. For example, the TBL1XR1 sequence of an amplified nucleic acid can be about 5 to about 2500 nucleotides in length (e.g., about 10 to about 2500 nucleotides in length, about 15 to about 2500 nucleotides in length, about 20 to about 2500 nucleotides in length, about 25 to about 2500 nucleotides in length, about 20 to about 1000 nucleotides in length, about 20 to about 500 nucleotides in length, or about 50 to about 100 nucleotides in length), and the TP63 sequence of that amplified nucleic acid can be about 5 to about 2500 nucleotides in length (e.g., about 10 to about 2500 nucleotides in length, about 15 to about 2500 nucleotides in length, about 20 to about 2500 nucleotides in length, about 25 to about 2500 nucleotides in length, about 20 to about 1000 nucleotides in length, about 20 to about 500 nucleotides in length, or about 50 to about 100 nucleotides in length). In some cases, the combined length of the TBL1XR1 and TP63 sequences that are amplified can be between about 50 and about 5000 nucleotides (e.g., between about 75 and about 5000 nucleotides, between about 100 and about 5000 nucleotides, between about 250 and about 5000 nucleotides, between about 500 and about 5000 nucleotides, between about 50 and about 2500 nucleotides, between about 500 and about 2500 nucleotides, or between about 50 and about 1000 nucleotides). In some cases, the primer pairs provided herein have the ability to amplify a junction region of a TBL1XR1 and TP63 gene rearrangement such as the junction region set forth in FIG. 1D.

Examples of particular primer pairs for amplifying a TBL1XR1 and TP63 gene rearrangement provided herein include, without limitation, the following primer pairs:

```
Pair 1:
Forward:
                                      (SEQ ID NO: 1)
CAGTGGCTCTACACAGTTAG Reverse:
                                      (SEQ ID NO: 2)
TGGGTAGTCGGTGTTG Pair 2:
Forward:
                                      (SEQ ID NO: 3)
AGAAGGAGGGCAAGATGTTC Reverse:
                                      (SEQ ID NO: 4)
TTCTGAATCTGCTGGTCCAT
```

This document also provides isolated nucleic acid molecules having (a) a TBL1XR1 nucleic acid sequence and (b) a TP63 nucleic acid sequence. The isolated nucleic acid molecules provided herein can be any appropriate length including, without limitation, lengths ranging from about 50 and about 5000 nucleotides (e.g., between about 75 and about 5000 nucleotides, between about 100 and about 5000 nucleotides, between about 250 and about 5000 nucleotides, between about 500 and about 5000 nucleotides, between about 50 and about 2500 nucleotides, between about 500 and about 2500 nucleotides, or between about 50 and about 1000 nucleotides).

This document also provides FISH assays for detecting the presence or absence of a TBL1XR1 and TP63 gene rearrangement. For example, the FISH assays described herein can be used to detect the presence or absence of a TBL1XR1 and TP63 gene rearrangement.

As described herein, the primer pairs and isolated nucleic acid molecules provided herein as well as the FISH assays and PCR-based assays provided herein can be used to determine whether or not a patient has cancer with a TBL1XR1 and TP63 gene rearrangement or a dominant negative TP63 phenotype. For example, a patient sample (e.g., a T cell lymphoma sample) can be assessed for the presence or absence of a TBL1XR1 and TP63 gene rearrangement using a primer pair provided herein or an isolated nucleic acid that was amplified using an amplification reaction.

This document also provides methods and materials for treating cancer patients having a cancer with a TBL1XR1 and TP63 gene rearrangement or a dominant negative TP63 phenotype. For example, patients identified as having cancer cells (e.g., T-cell lymphoma cells) with a TBL1XR1 and TP63 gene rearrangement or that express a dominant-negative form of TP63 can be treated with cisplatin and/or PARP inhibitors to decrease the amount of dominant-negative form of TP63 in the tumor cells.

In some cases, a TP63 gene rearrangement (e.g., translocation) that involves TP63 nucleic acid and nucleic acid other than TBL1XR1 nucleic acid, such as FOXK2 nucleic acid (see, e.g., GenBank® Accession No. NM_004514.3 and GI No. 109702898) or ATXN1 nucleic acid (see, e.g., GenBank® Accession No. NM_000332.3 and GI No. 189491746), can be used as described herein in place of or in addition to a TBL1XR1 and TP63 gene rearrangement. For example, cisplatin and/or PARP inhibitors can be used to treat cancer patients having a cancer with a FOXK2 and TP63 gene rearrangement.

In some cases, fluorescence in situ hybridization and/or break-apart fluorescence in situ hybridization techniques can be used to identify TBL1XR1 and TP63 gene rearrangements or gene rearrangements involving TP63 (e.g., FOXK2 and TP63 gene rearrangements). For example, break-apart fluorescence in situ hybridization techniques can be used to identify translocations that involve TP63 nucleic acid any other appropriate nucleic acid partner (e.g., a TBL1XR1 nucleic acid or a FOXK2 nucleic acid).

The invention will be further described in the following examples, which do not limit the scope of the invention described in the claims.

EXAMPLES

Example 1

Figure 1B:
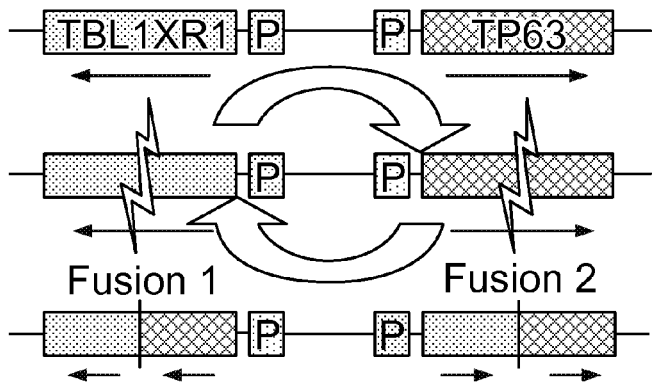
FIG. 1B is a schematic diagram of inv(3), which creates two unique gene fusions. "P" indicates promoter region.
Figure 1C:
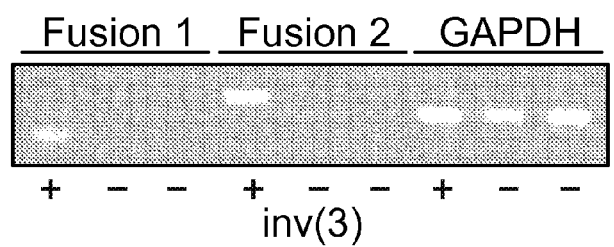
FIG. 1C is a photograph of RT-PCR results showing the expression of the two fusion products, consistent with the known high activity of the TBL1XR1 promoter.

Translocation Involving TP63 and TBL1XR1 Nucleic Acid Results in a Dominant Negative TP63 Isoform A recurrent inv(3)(q26q28) that fuses TBL1XR1 to the TP53 homologue, TP63, was discovered in PTCLs. Using genome-wide mate-pair NGS as described elsewhere (Feldman et al., Blood, 117(3):915-919 (2011)), PTCLs (2/14; 14%) with TBL1XR1/TP63 fusion on chromosome 3 were identified (FIG. 1A). Using PCR and Sanger sequencing (not shown), an inv(3)(q26q28) with the formation of two putative fusion genes was demonstrated (FIG. 1B). RT-PCR revealed that both fusion transcripts were present, with a particularly strong band for fusion 2, predicted to utilize the highly active TBL1XR1 promoter (FIG. 1C). Sanger sequencing revealed an in-frame fusion with identical breakpoints in both cases discovered by NGS and an additional case identified subsequently (FIG. 1D). The fusion transcript encoded a ΔNp63 lacking a transactivation domain but containing DNA-binding and oligomerization domains (FIG. 1E). PTCLs with inv(3) had 28-fold higher expression of TP63 than PTCLs without inv(3) by quantitative PCR. TBL1XR1 expression was high in both groups (FIG. 1F). Western blot using anti-C-terminal p63 demonstrated a 100 kD band consistent with the predicted TBL1XR1-ΔNp63 fusion protein in a PTCL with inv(3), but not in Karpas 299, a PTCL cell line that expresses p63 but lacks inv(3) (FIG. 1G).

Figure 3:
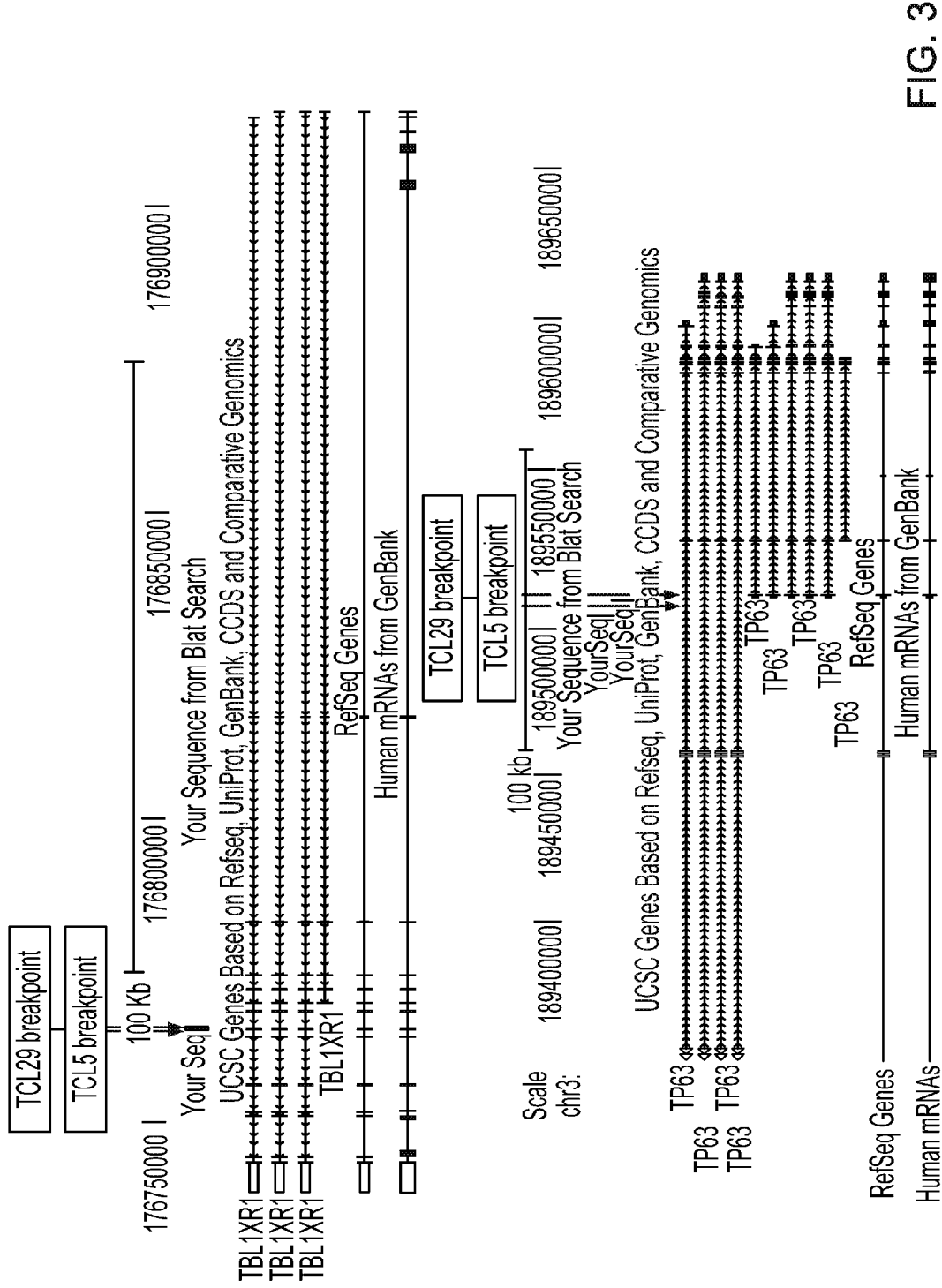
FIG. 3 contains schematics showing the positions of the TCL5 and TCL29 breakpoints at the genomic DNA level.
Figure 4:
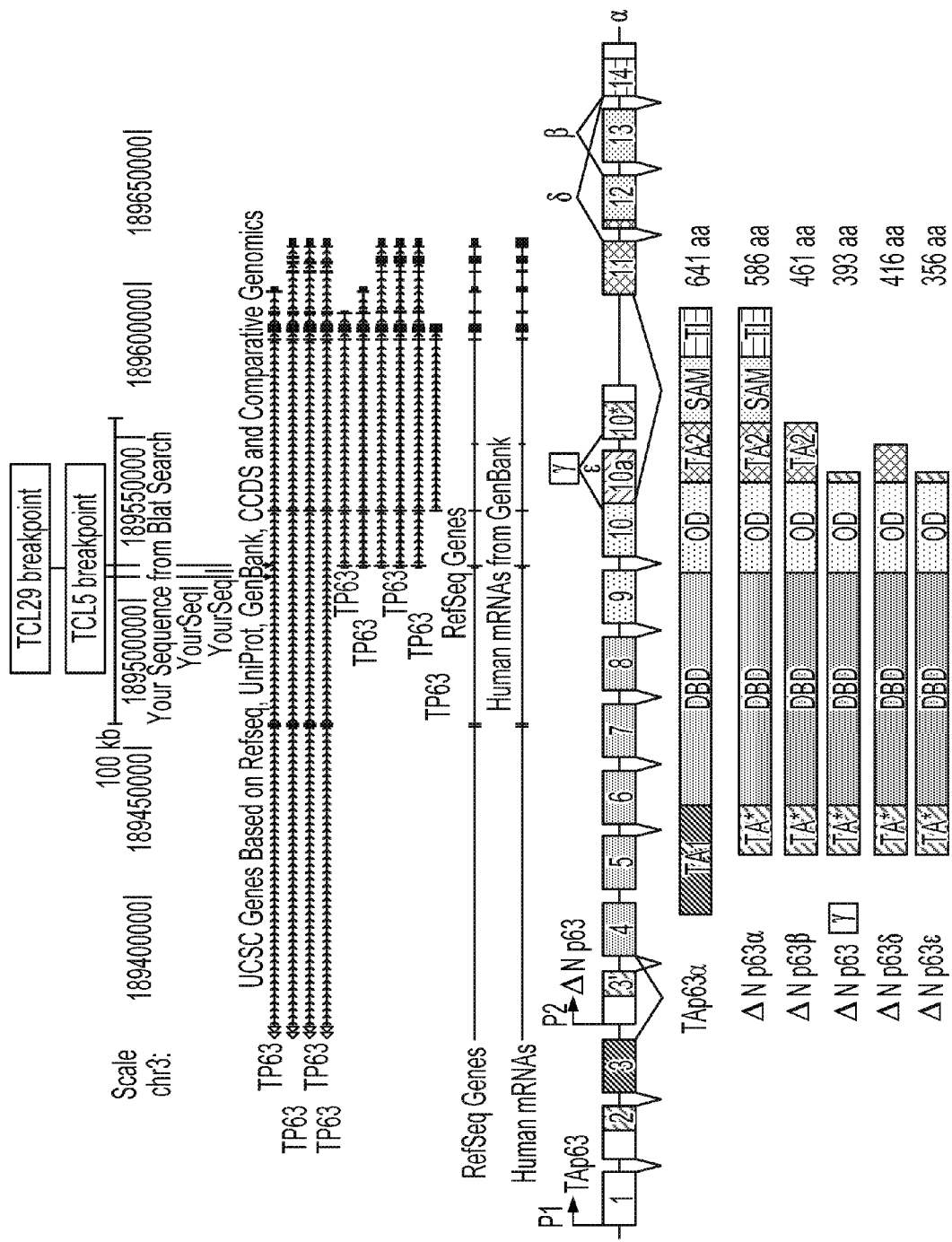
FIG. 4 contains schematics showing the breakpoints in TP63, which correspond to the beginning of the DNA-binding domain (DBD) and exclude the transactivation (TA) domain present in the full-length TAp63 isoform. Instead, the inv(3) results in a truncated form at the N-terminus (ΔNp63) with a dominant negative function.

PCR and Sanger sequencing identified the breakpoints on both minus and plus strands corresponding to the inv(3)(q26q28) (FIG. 2). These breakpoints differed slightly for both the TP63 and TBL1XR1 genes (FIG. 3), but because of their intronic location predicted formation of an identical fusion transcript. The breakpoints in the TP63 gene were immediately upstream of the DNA encoding the DNA-binding domain of the p63 protein (FIG. 4).

Figure 5A:
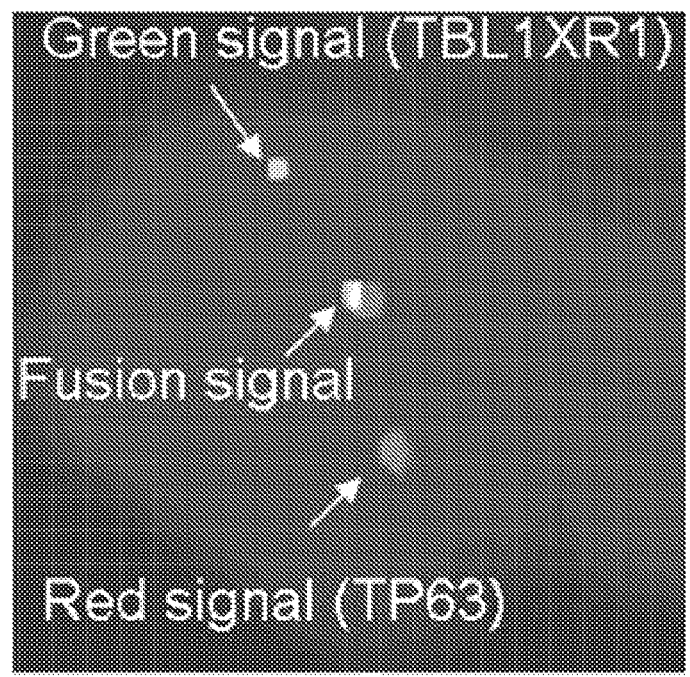
FIGS. 5A-C demonstrate that PTCLs with inv(3) lack other known genetic abnormalities. Translocations of ALK or IRF4 were assessed by fluorescence in situ hybridization (FISH), NGS, and/or immunohistochemistry.

Few genetic abnormalities in PTCLs have been identified. The only recurrent translocations seen in >1% of cases are those involving ALK (discovered in the 1980's), and those involving IRF4 recently discovered (FIG. 5A). TP53 mutations are rare in PTCLs, in contrast to many other cancers. ALK translocations inhibit the p53 pathway, but mechanisms for p53 dysregulation in ALK-negative PTCLs remain unknown.

Figure 5B:
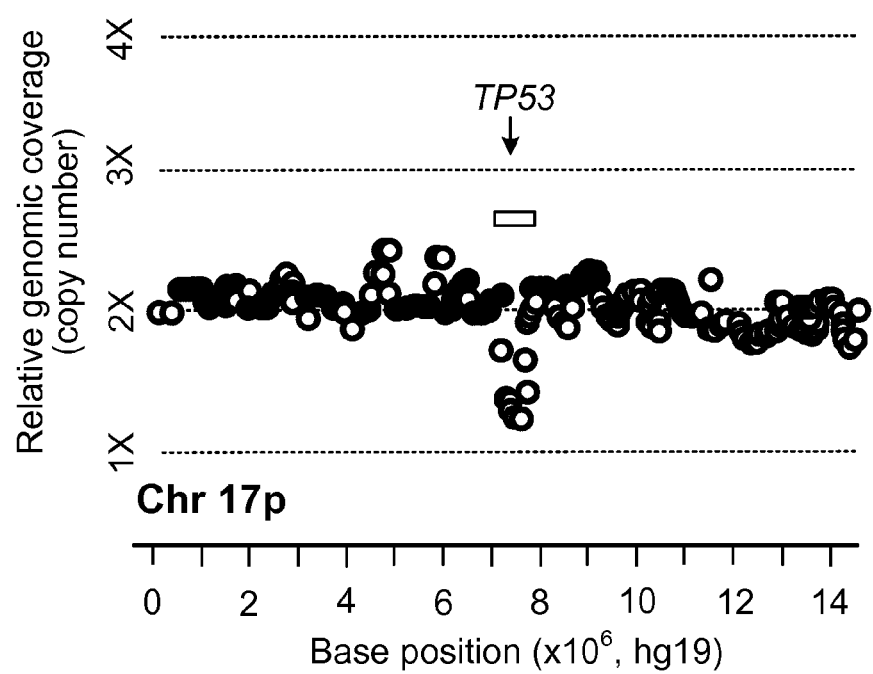
Figure 5C:
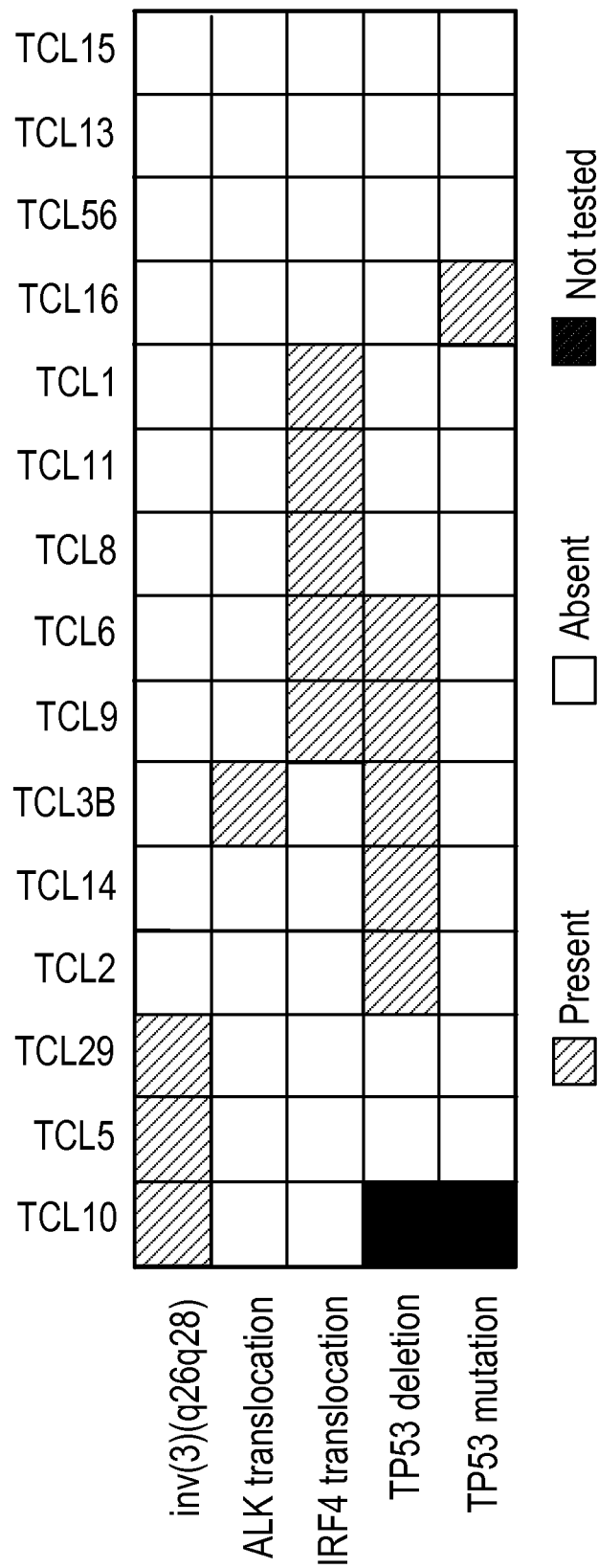

The NGS data was analyzed to identify TP53 deletions in PTCLs by using locus-specific genomic coverage to assess copy number as well as sequence analysis to identify the re-joined borders of the deleted region (FIG. 5B). TP53 deletions were identified in 5/14 (36%) of cases (FIG. 5C). As expected, TP53 mutations were rare. Importantly, cases with inv(3) lacked other known mechanisms of p53 dysregulation (e.g., deletion, mutation, or ALK translocation). This suggests inv(3) may be a recurrent genetic cause of p53 pathway dysregulation in PTCLs through effects of the resultant ΔNp63 on p53 or its homolog, p73.

Figure 6:
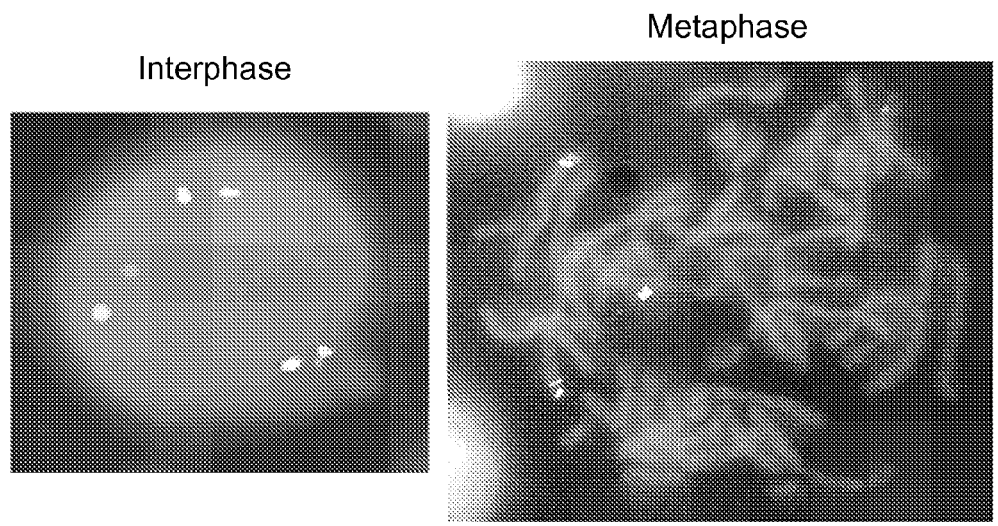
FIG. 6 contains images of interphase and metaphase FISH using an inv(3)(q26q28) probe.
Figure 19:
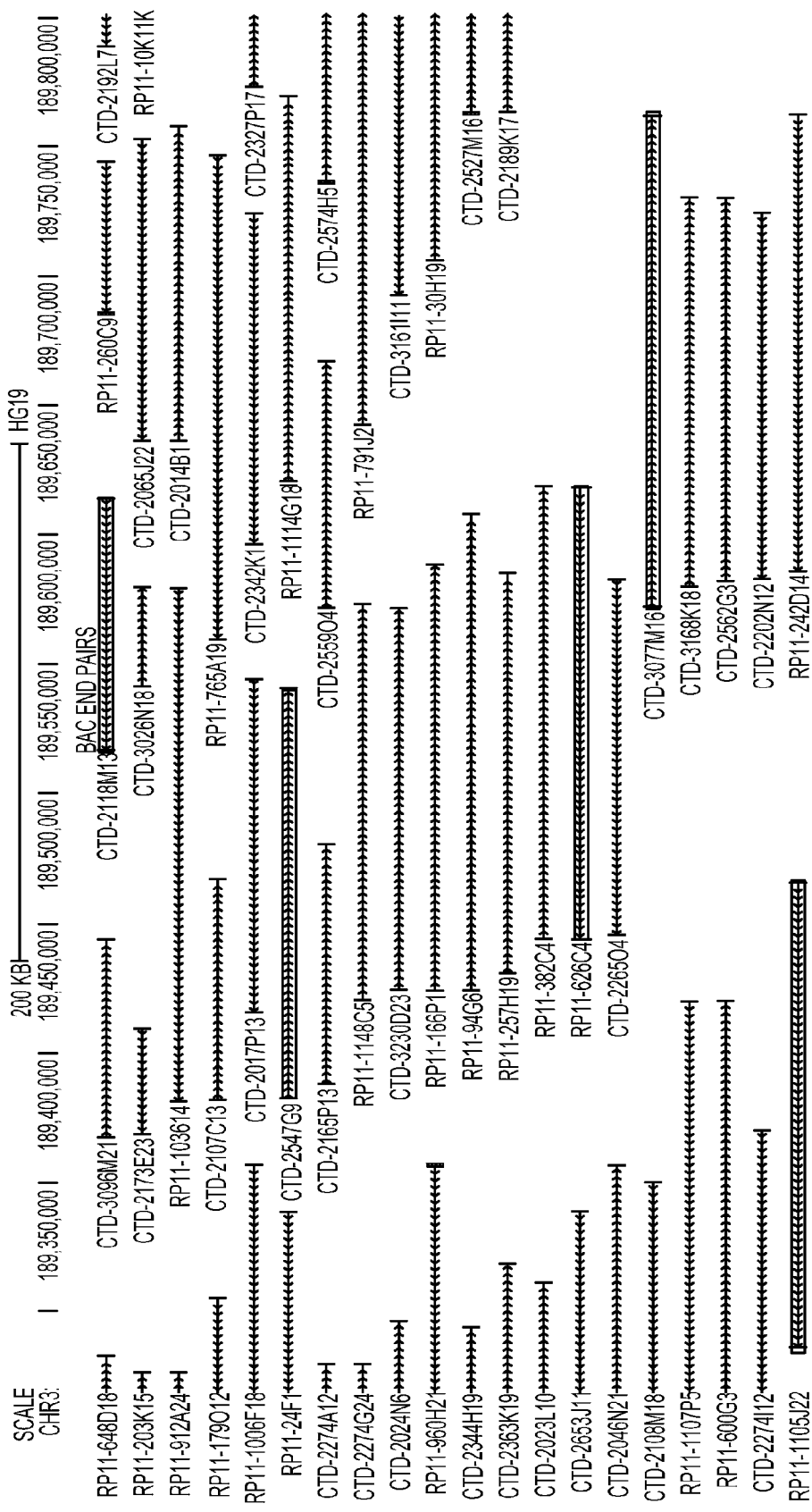
FIG. 19 is a graph plotting the location of the indicated BAC clones.
Figure 19:
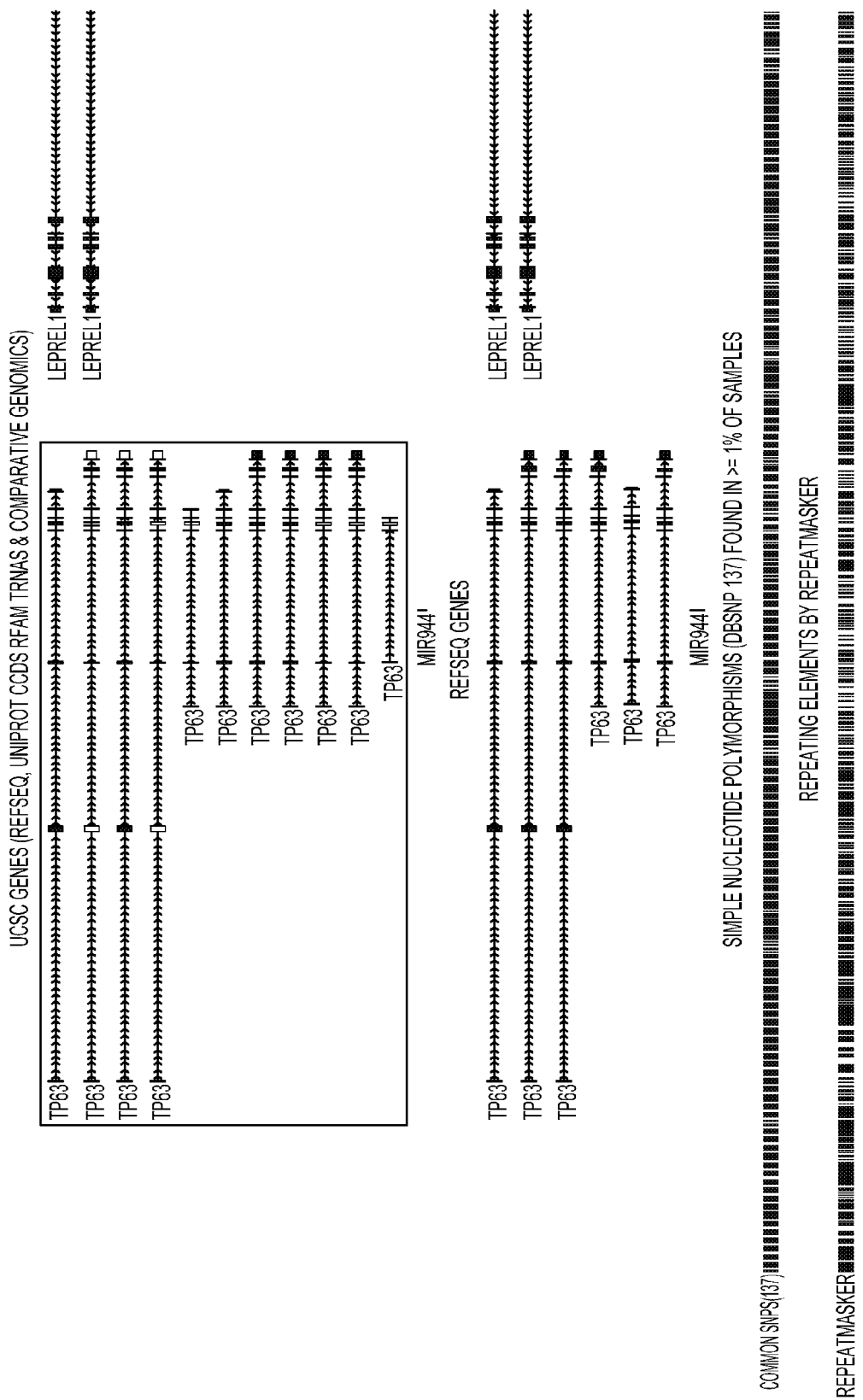

A dual-fusion fluorescence in situ hybridization probe was developed to detect the inv(3)(q26q28) as follows. For the TP63 locus, labeled in red/orange, bacterial artificial chromosomes (BACs) RP11-1105J22, RP11-626C4, and CTD-3077M16 (total probe size, 476 kb) were used (FIG. 19). In some cases, a dual-fusion fluorescence in situ hybridization probe was developed to detect the inv(3)(q26q28), whereby for the TP63 locus, bacterial artificial chromosomes (BACs) RP11-1105J22, CTD-3077M16, CTD-2547G9, and CTD-2118M13 were labeled and used (FIG. 19). For the TBL1XR1 locus, labeled in green, BACs RP11-1148M8, RP11-1012L11, CTD-2316F21, and RP11-994L2 (total probe size, 495 kb) were used. Preparation of the dual-fusion probe and hybridization to samples was performed using standard techniques described elsewhere (Patnaik et al., European J. Haemat., 84(6):518-524 (2010) and Feldman et al., Am. J. Clin. Pathol., 130(2):178-185 (2008)). Examples of metaphase and interphase FISH are shown in FIG. 6.

Figure 7:
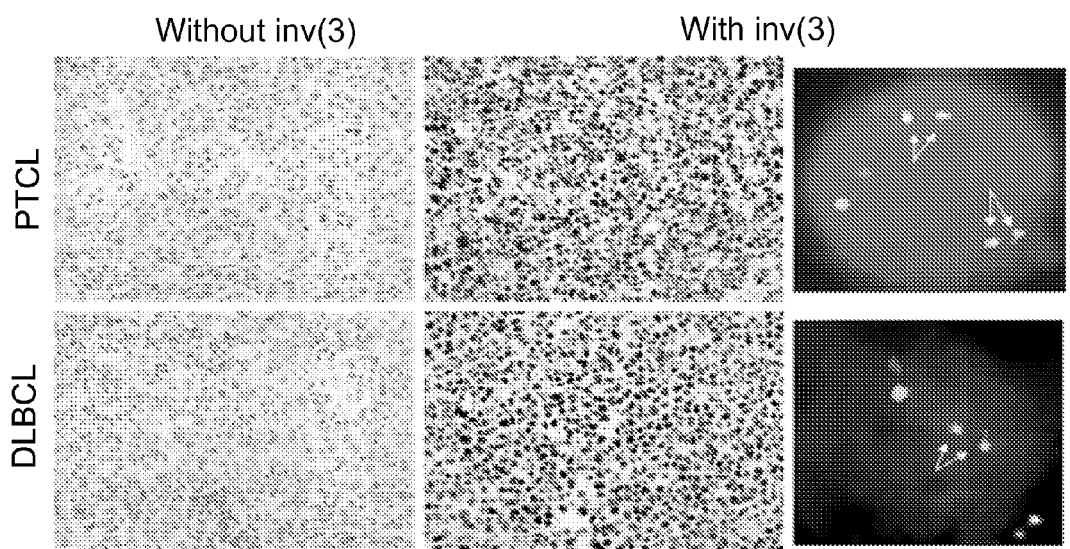
FIG. 7 contains photographs of immunohistochemistry results. C-terminal p63 is negative in most PTCLs and DLBCLs (left-hand panels). In contrast, cases with the inv(3)(q26q28) exhibit strong nuclear staining (middle panels). A dual-fusion interphase FISH probe was developed to detect inv(3) in paraffin tissue sections (right-hand panels). The normal chromosome 3 exhibits separated red and green signals. The inv(3) is represented by two abnormal fusion signals in proximity, as indicated by the pairs of arrows. The PTCL in the upper right panel has two copies of the abnormal chromosome 3 containing the inv(3).

PTCLs that exhibited the inv(3) by FISH revealed very strong nuclear expression of p63 protein by immunohistochemistry (FIG. 7, top). A similar association was found in diffuse large B-cell lymphoma (DLBCL; FIG. 7, bottom). The FISH probe also was able to identify PTCLs that had extra copies of the intact TP63 locus, without evidence of inv(3).

Figure 8:
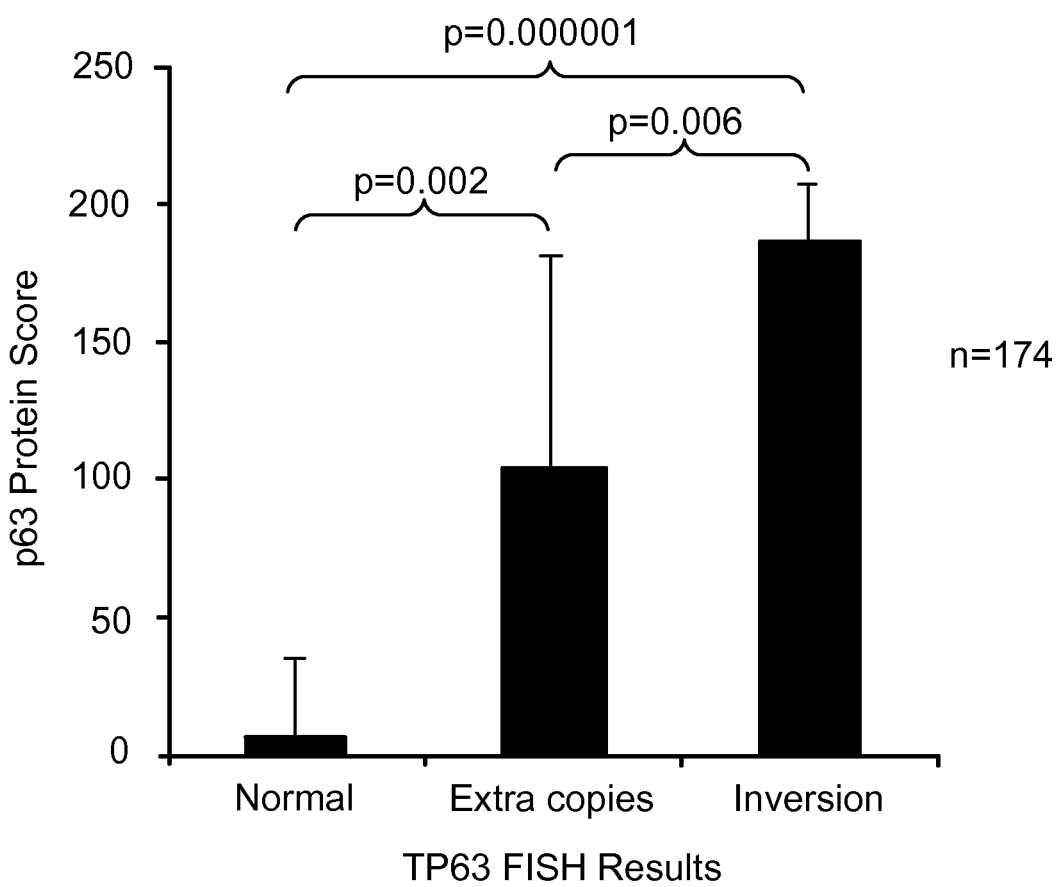
FIG. 8 is a graph plotting the association between immunohistochemistry (IHC) for p63 protein expression and FISH for presence of the inv(3). The p63 protein score was obtained by multiplying the percent of tumor cell nuclei positive by either 1 for weak staining or 2 for strong staining, resulting in a score ranging from 0 to 200. Cases with inversion all had uniform, strong cases, while most (but not all) cases with a normal FISH result were negative for p63. Cases with extra copies of TP63, but without inv(3), had a broad range of p63 protein scores, with a mean intermediate between the normal cases and the cases with inv(3). P values shown are from t test.
Figure 9:
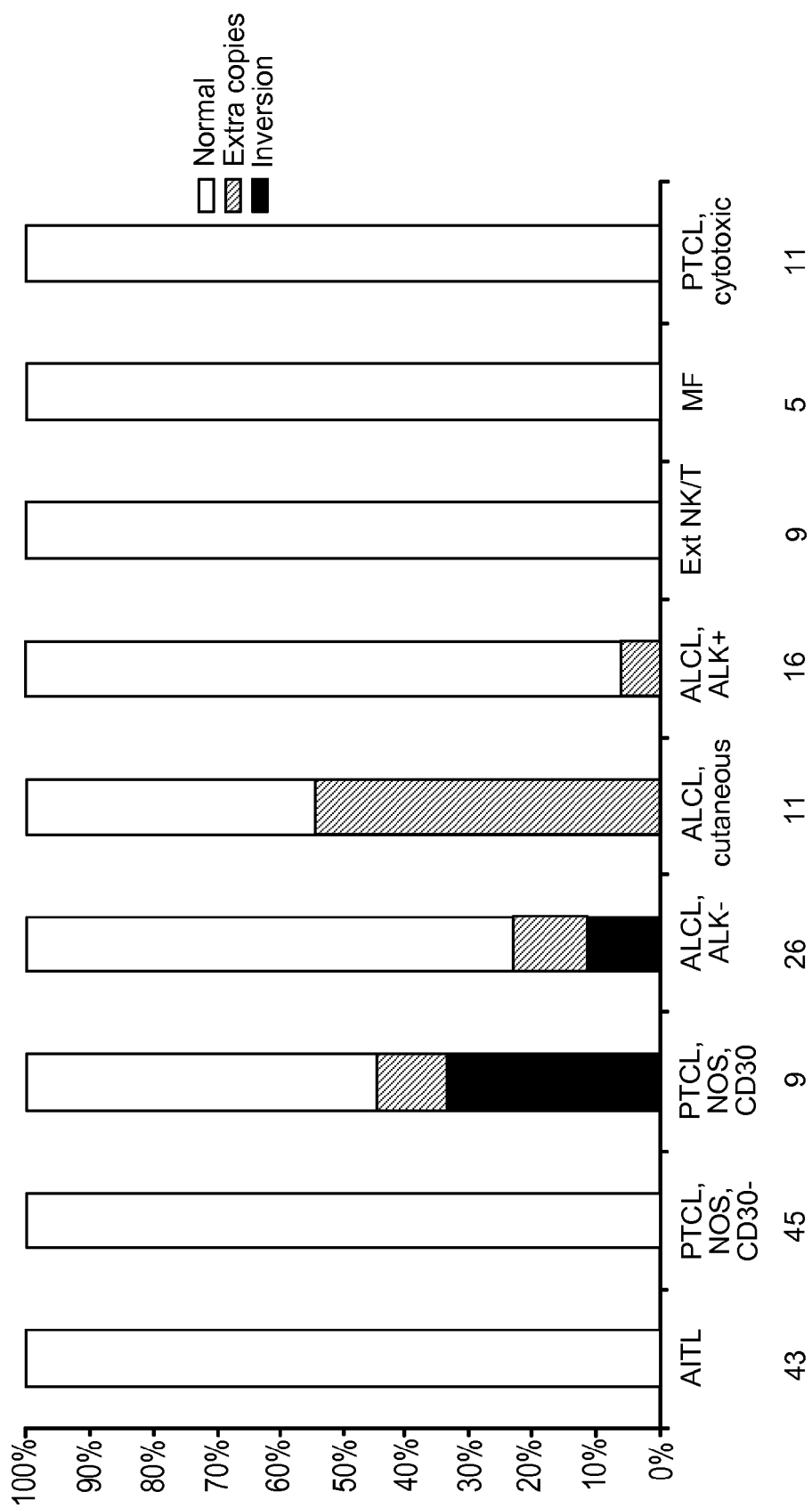
FIG. 9 is a graph plotting the association between FISH status and PTCL subtype in 175 patients. Numbers below are n in each group. All cases with inv(3) were either CD30-positive PTCL-NOS cases or ALK-negative ALCL cases. Extra copies of TP63 were observed in these two subtypes as well as in cutaneous ALCL and rarely in ALK-positive ALCL.

The correlation between these abnormalities was examined by developing a protein staining score as shown in FIG. 8. The inv(3) was associated with consistently high protein scores whereas cases normal by FISH were almost always p63 negative. Cases with extra copies sometimes had very high scores and sometimes were negative, with a mean protein score intermediate between scores for cases with inv(3) and scores for cases with normal FISH. Thus, strong expression by immunohistochemical staining was not a surrogate for FISH to detect inv(3) because some cases with strong staining had extra copies of TP63 and rare cases had normal FISH. The relationship between FISH and the PTCL subtype was assessed (FIG. 9). All cases with the inv(3) were either CD30-positive PTCL-NOS or ALK-negative ALCL. These diseases are known to have a worse prognosis than CD30-negative PTCL-NOS or ALK-positive ALCL, respectively.

Figure 10:
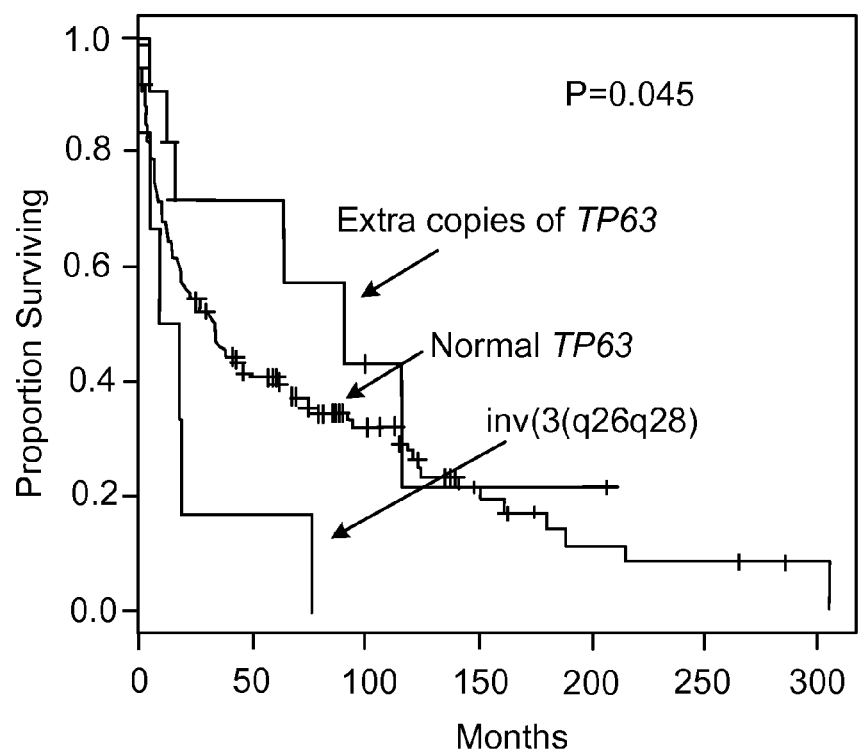
FIG. 10 is a graph plotting Kaplan-Meier survival curves of patients with T-cell lymphoma from time of diagnosis, stratified based on result of FISH for inv(3)(q26q28). Overall survival was significantly reduced for patients with inv(3). P=0.045, inv(3) vs. no inv(3).
Figure 11:
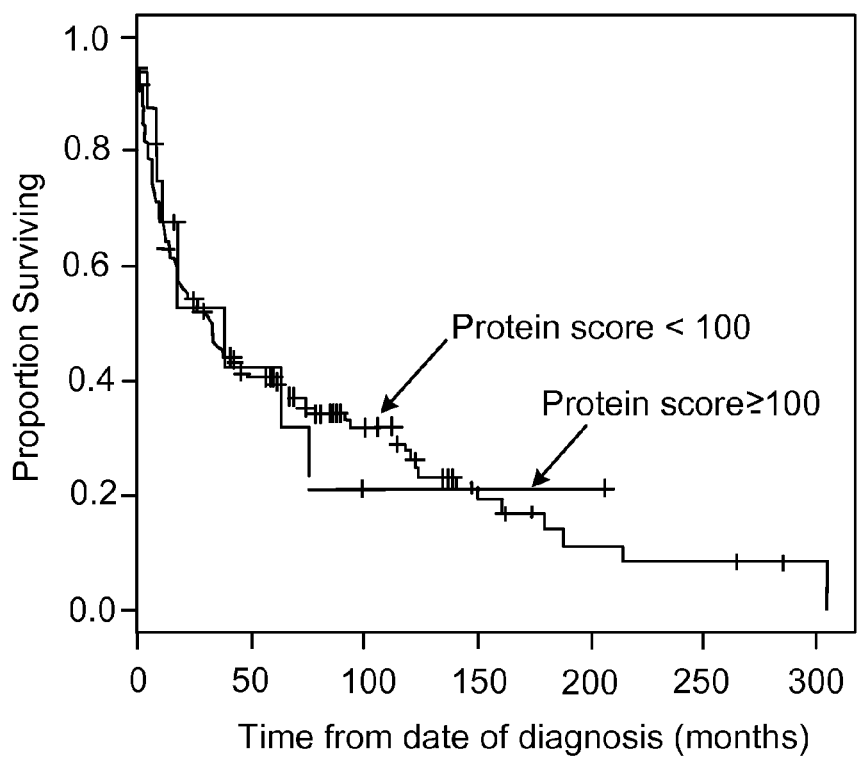
FIG. 11 is a graph plotting Kaplan-Meier survival curves of patients with T-cell lymphoma from time of diagnosis, stratified based on result of immunohistochemistry for p63 (4A4 antibody), scored as described for FIG. 8. There is no significant difference in overall survival between the two groups.

The inv(3) was observed in PTCLs that are positive for CD30 and negative for ALK (Table 1). Finally, PTCLs with the inv(3) had poorer overall survival times than cases with normal FISH results or those with extra copies of the TP63 locus (FIG. 10). This difference in survival was not seen based on p63 immunohistochemistry alone (FIG. 11), emphasizing the potential prognostic utility of a FISH test.

TABLE 1

Phenotype (immunohistochemical positivity for CD30 or ALK) correlates with result of TP63 FISH in T-cell lymphomas.

|  | CD30 (% positive) | ALK (% positive) |
| --- | --- | --- |
| Inversion | 100.0 | 0.0 |
| Extra copies | 100.0 | 9.1 |
| Normal | 28.3 | 9.4 |

Figure 12:
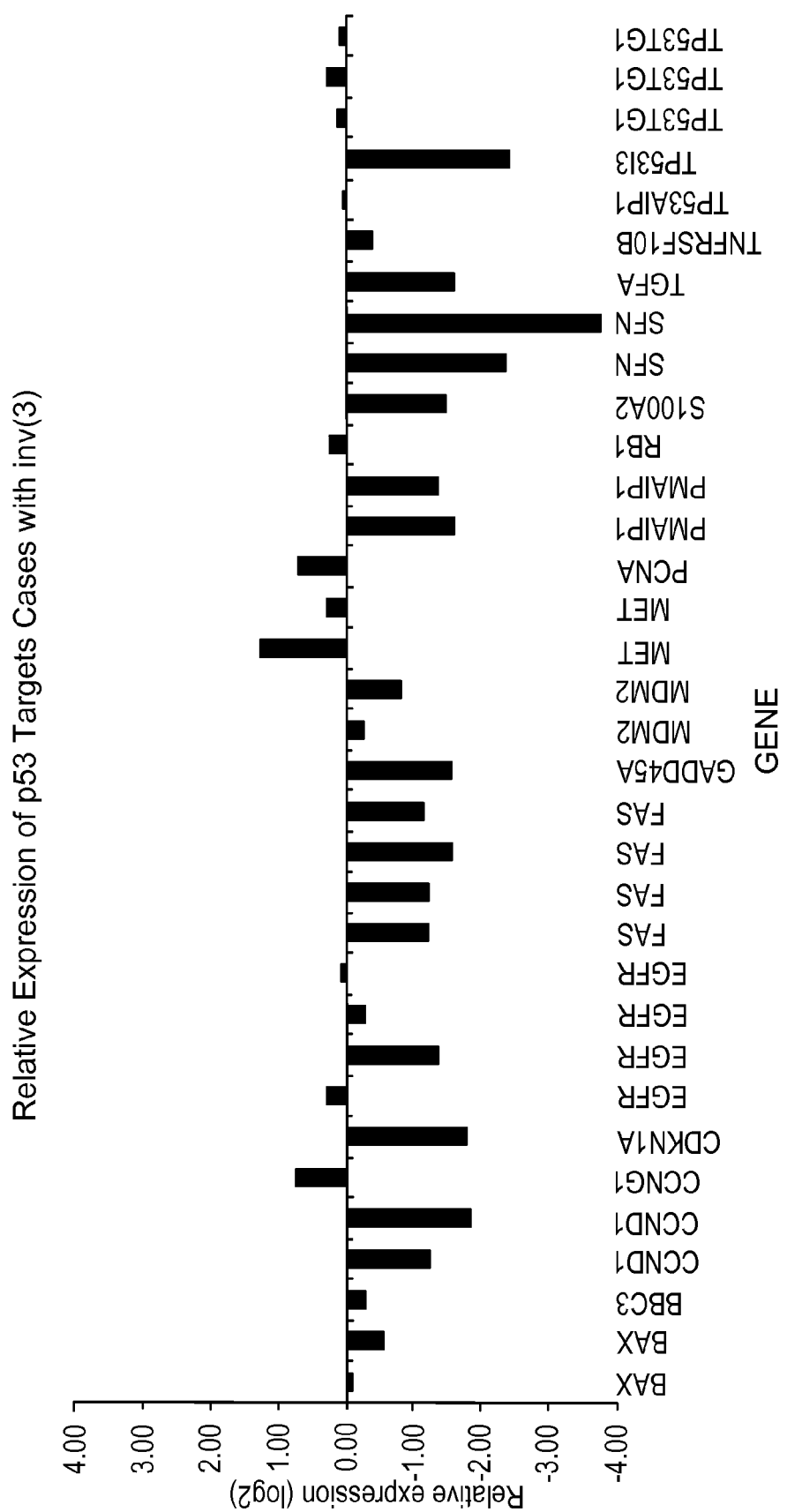
FIG. 12 is a graph plotting the transcriptional targets activated by p53 based on data from gene expression profiling of PTCLs. Relative expression in cases with inv(3) compared to those without inv(3) indicates lower expression of most genes, suggesting inv(3) correlates with decreased p53 transcriptional activity.
Figure 13:
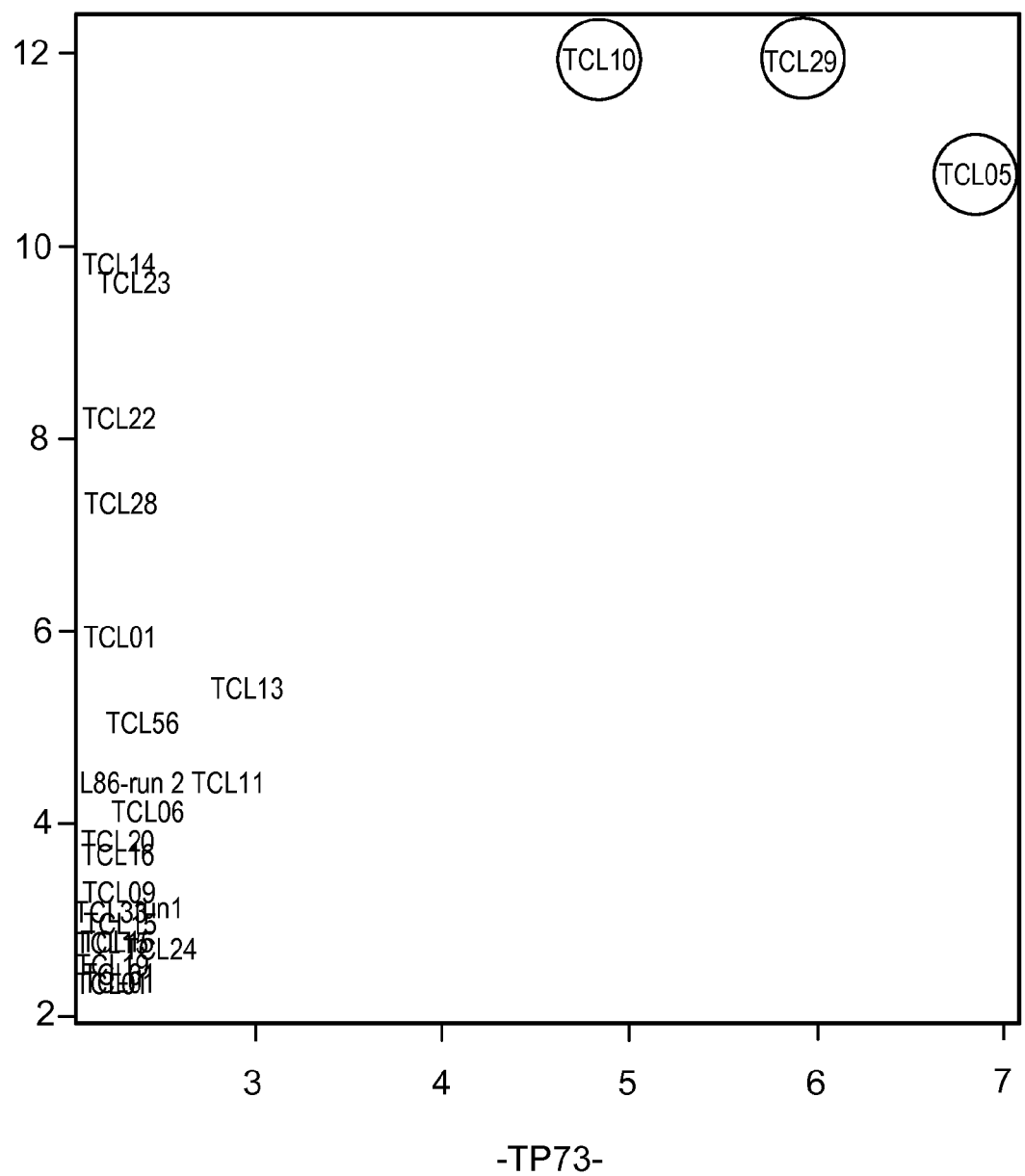
FIG. 13 is a graph plotting a correlation between expression of TP63 and TP73 based on data from Affymetrix-based gene expression profiling. Circled case numbers have the inv(3), whereas those without circles lack the inv(3). TP63 and TP73 both were highly expressed in cases with inv(3).

Using gene expression profiling (Affymetrix), PTCLs with inv(3) were shown to down-regulate many genes known to be expressed as a result of p53 transcriptional activity (FIG. 12). These data suggest a relationship between the inv(3) and p53 function. As mentioned above, p63 may also interact with the p53 homologue, p73, as demonstrated in breast cancer and SCC. A correlation was observed among presence of inv(3), expression of TP63, and expression of TP73 in PTCL (FIG. 13). It is possible that the inv(3) may represent either a biomarker or a therapeutic target in these diseases as well.

Figure 14:
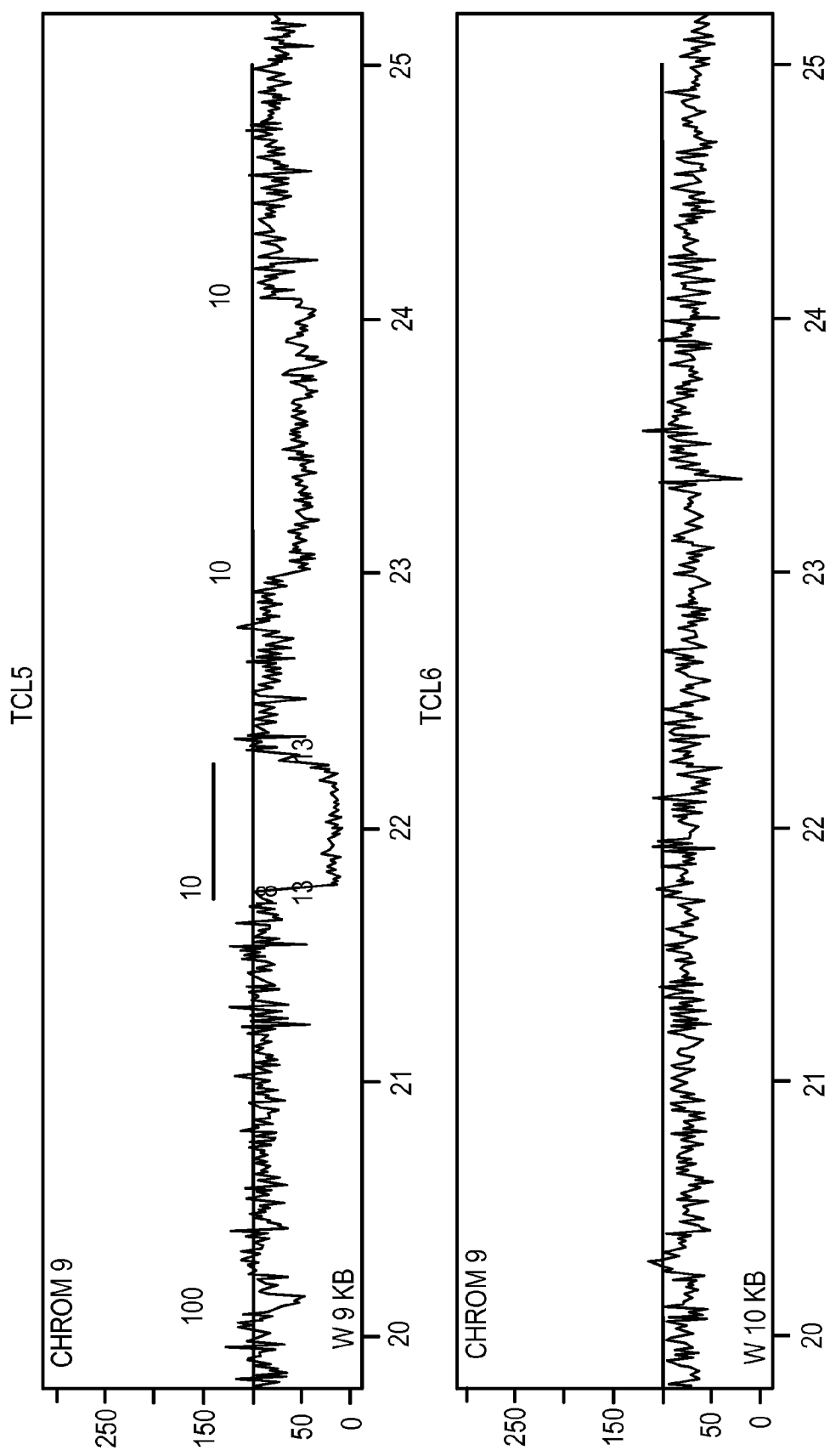
FIG. 14 contains graphs plotting an assessment of copy number of CDKN2A using frequency plots based on next generation sequencing data (similar to that shown in FIG. 5B). TCL5 has inv(3), and TCL6 lacks inv(3). In the top plot from TCL5, the horizontal bar represents aberrant mate pair sequences spanning the CDKN2A locus. The tracing below represents genomic coverage, proportional to copy number. The >50% decrease in the area under the horizontal bar indicates a homozygous CDKN2A deletion. TCL6 has no CDKN2A deletion.
Figure 15:
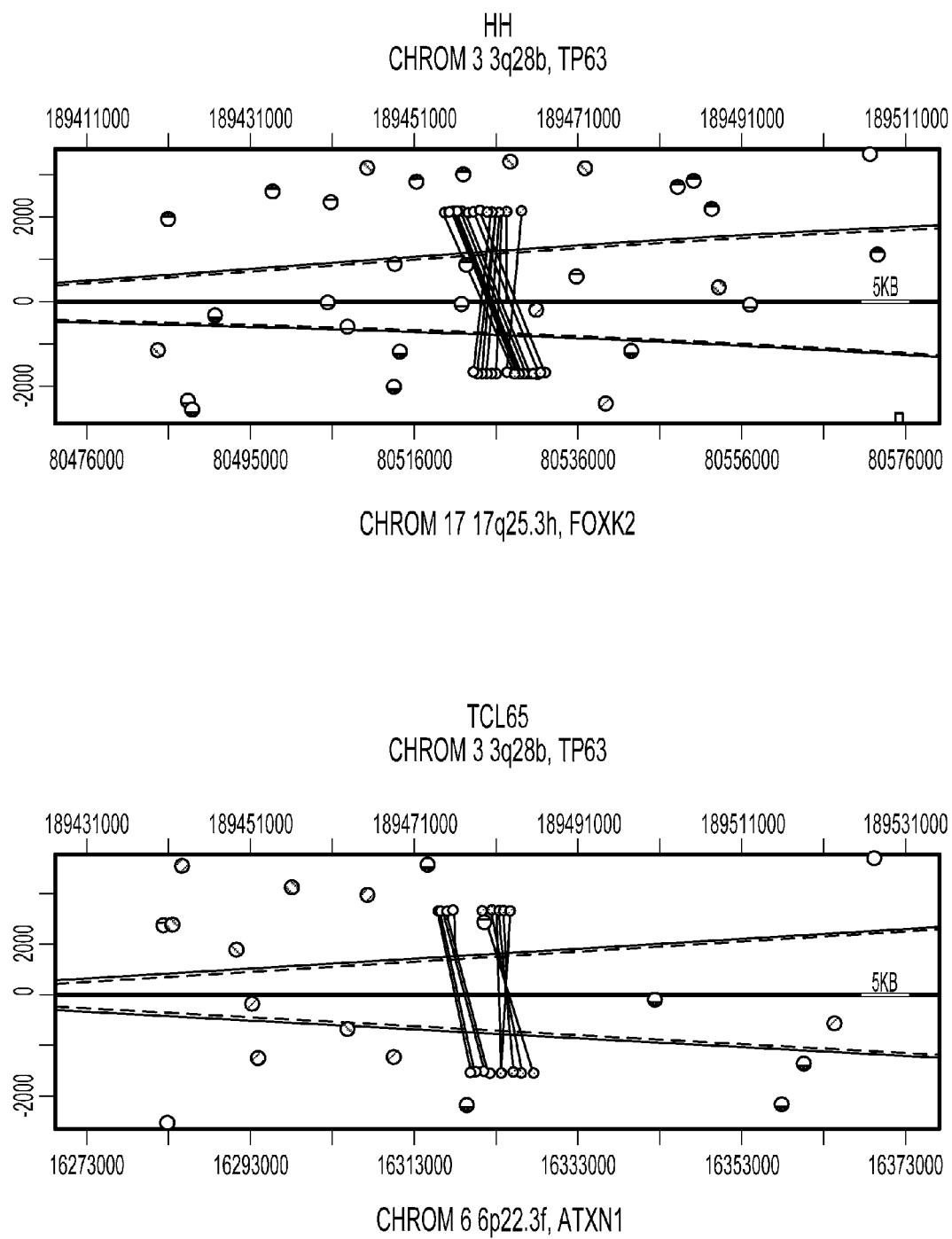
FIG. 15 contains graphs of mate-pair next-generation sequencing data demonstrating translocations between TP63 and alternate gene partners. On the left, an aggressive cutaneous PTCL (non-MF/SS) cell line, HH, has a t(3;17) involving TP63 and FOXK2. On the right, a tissue specimen from a patient with PTCL-NOS shows a t(3;6) involving TP63 and ATXN1. Both translocations have 3p28 breakpoints immediately 5' of the DNA binding domain-encoding portion of the TP63 gene, and thus generate ΔNp63-containing fusion proteins similar to the inv(3). The finding of these two additional cases among 16 additional cases studied indicates that additional TP63 partners likely exist. In addition to next generation sequencing, the TP63 FISH strategy can detect these variants by altering the labeling of the BAC DNA to generate a breakapart probe for TP63 that can identify rearrangements independent of the partner locus.
Figure 16:
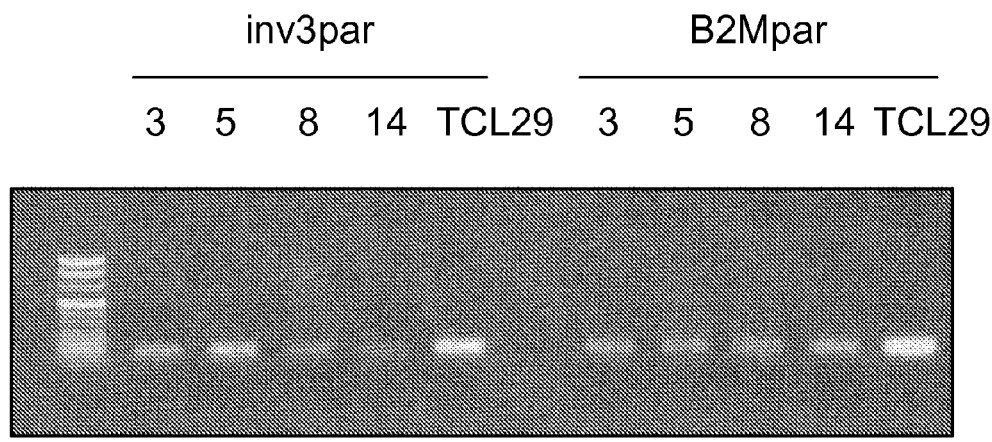
FIG. 16 provides results from an additional method for detecting inv(3) in paraffin material. Primers were designed around the breakpoint in the fusion transcript from TBL1XR1/TP63 (top panel). RNA was extracted from paraffin material, converted to cDNA using poly-d(T) primers, and subjected to 40 cycles of PCR using these primers (or primers to beta-2 microglobulin as a control)(middle panel). A 108-base pair amplicon indicates the presence of the inv(3). In this example, cDNA from all of the lanes was then subjected to Sanger sequencing using the same inv3par primers. All cases exhibited the identical amplicon spanning the breakpoint (bottom panel), with nucleotides in gray derived from TBL1XR1 and those in black derived from TP63.

An additional finding in these cases was the coexistence of homozygous deletions of CDKN2A encoding p16 in cases with inv(3), which was not seen in any of the cases without inv(3). These data are shown in FIG. 14 and Table 2. Deletions of CDKN2A have been associated with up-regulation of TBL1XR1 in DLBCL, and this up-regulation might further enhance the expression of the TBL1XR1-TP63 fusion transcript (fusion 2) in cancers with inv(3).

TABLE 2

Relationship of inv(3) to CDKN2A deletion.

| Case or Cell line | inv(3)(q26q28) | CDKN2A (p16) Deletion |
| --- | --- | --- |
| TCL5 | yes | homozygous |
| TCL29 | yes | homozygous |
| TCL15 | no | hemizygous |
| TCL8 | no | no |
| TCL11 | no | no |
| FEPD | no | no |
| TCL1 | no | no |
| SR786 | no | hemizygous |
| SUDHL1 | no | hemizygous |
| K299 | no | no |
| TCL3B | no | no |
| TCL56 | no | no |
| TCL13 | no | no |
| TCL14 | no | no |
| TCL6 | no | no |
| TCL9 | no | no |
| Mac1/2A | no | no |
| TCL16 | no | no |
| TCL32 | no | no |
| TCL2 | no | no |

The consequences of the inv(3) on function of TBL1XR1 may contribute to the biology of PTCL, DLBCL, and other cancers with inv(3). As shown in FIGS. 1B and 1C, two fusion transcripts are generated by the inv(3). In addition to fusion 2 describe above, fusion 1, which combines the upstream portion of TP63 encoding the transactivation domain of p63 with the downstream portion of TBL1XR1, presumably under the control of the TP63 promoter, was also detected. This may also produce a novel fusion protein, and either of the two fusion proteins might alter the normal function of TBL1XR1 in its role as a component of the NCoR complex. Recurrent deletions or loss-of-function mutations of TBL1XR1 have been reported in follicular lymphomas, primary central nervous system lymphomas, and acute lymphoblastic leukemias.

Taken together, these results demonstrate that (a) the inv(3) is one of the three most common chromosomal rearrangements in PTCL discovered to date; (b) the inv(3) occurs in specific PTCL subtypes, namely PTCLs expressing CD30 but lacking expression of ALK; and (c) the inv(3) is associated with poor prognosis in PTCL.

Example 2

Additional Translocations Involving TP63

Figure 17:
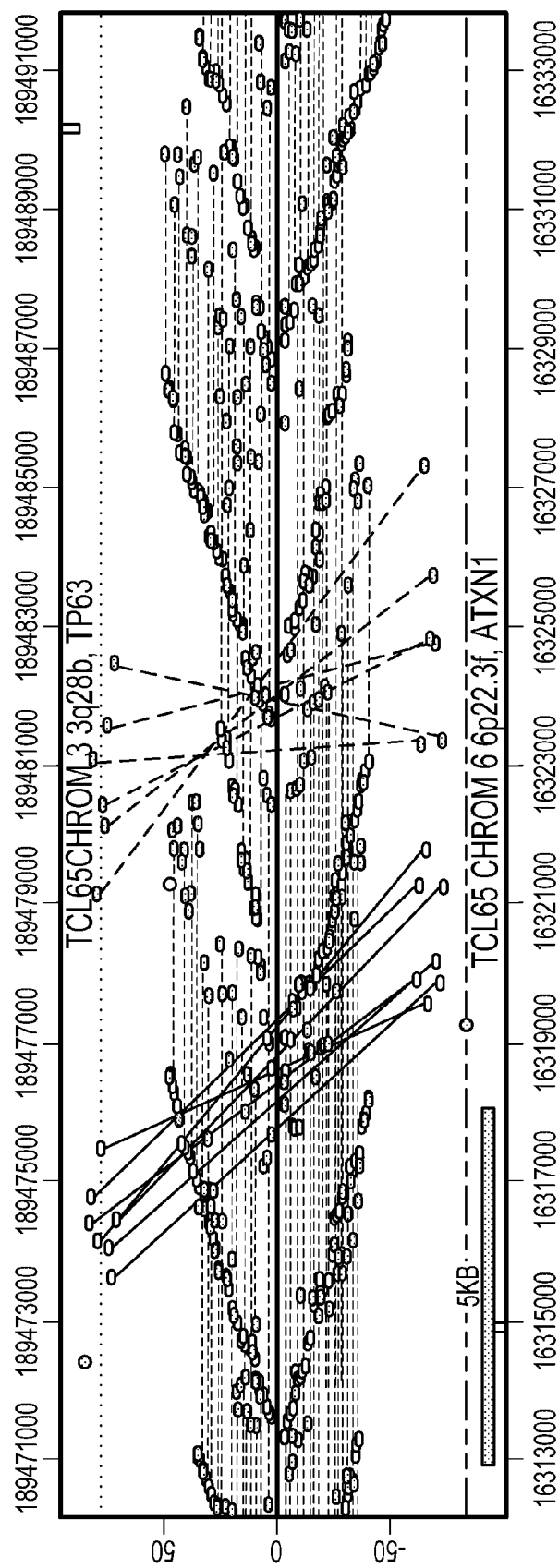
FIG. 17. Breakpoint 1 is centered on the top horizontal axis; while breakpoint 2 is centered on the bottom horizontal axis. All read pairs, both concordant and discordant, are shown for the plotted region. The read mapping to the DNA strands are shown as heavy dots. A line bridges the gap between concordant reads. The discordant read-pairs cross from the top to the bottom horizontal axis.
Figure 18:
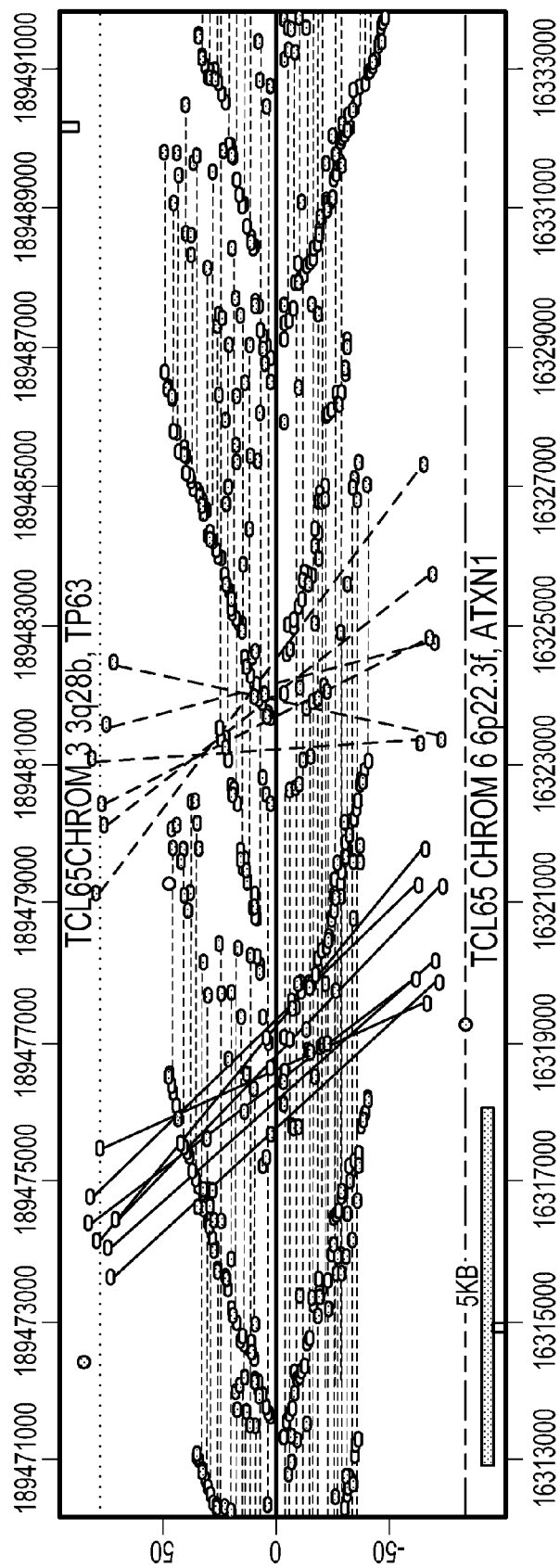
FIG. 18 shows the DNA aberration in the HH cell-line. This was a balanced translocation where the telomeric portions of the q arms of chromosome 3 and chromosome 17 were exchanged. The translocation resulted in two fusion genes involving segments of TP63 and FOXK2. Plots spanning junctions were generated to provide a visual of the mapping of mate-pair reads across a junction points. This fusion product was also validated by Western blot.

Additional translocation (inter-chromosomal) events involving TP63 were identified. Case TCL65 had a balanced translocation where the telomeric portion of the q arm of chromosome 3 was exchanged with the telomeric portion of the p arm of chromosome 6. The translocation results in two fusion genes involving segments of TP63 and ATXN1. Plots spanning junctions were generated to provide a visual of the mapping of mate-pair reads across a junction points. The junction plot shown in FIG. 17 displays the concordant and discordant read-pairs in the region of the rearrangement. The pattern of the discordant read pairs gave an indication of the type of rearrangement, such as a balanced or unbalanced translocation, deletion or inversion. In this case, it appeared as a balanced exchange of the p and q arms. FIG. 18 displays a TP63 related DNA aberration in the HH cell-line. This is a balanced translocation where the telomeric portions of the q arms of chromosome 3 and chromosome 17 were exchanged. The translocation will result in two fusion genes involving segments of TP63 and FOXK2. One of the reads hit exactly on the junction point (5'-TAAAAAAACATCTAAA-CTACAAGATATTC-CTAACAACGTAGAAATCCTGGGGCTTCTCTTGCCT-TATGA CTATTCCAACATTTTTATATTCTCATATATG-3'; SEQ ID NO:5). This fusion product was also validated by western blot.

Taken together, these results demonstrate that portions of TP63 fused with portions of other genes (e.g., TBL1XR1, ATXN1, and FOXK2) can be expressed in PTCL and can result in aggressive disease. These results also demonstrate that cancer patients identified as having a portion of TP63 fused with a portion of another gene can be identified as having an aggressive form of cancer and can be treated accordingly.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition for performing dual-fusion fluorescence in situ hybridization, wherein said composition comprises a first nucleic acid probe comprising a first fluorescence label and a second nucleic acid probe comprising a second fluorescence label, wherein said first and second fluorescence labels are different, wherein said first nucleic acid probe lacks said second fluorescence label, wherein said second nucleic acid probe lacks said first fluorescence label, wherein said first nucleic acid probe comprises a nucleic acid molecule comprising at least 10 Kb of the TP63 nucleotide sequence present in bacterial artificial chromosome CTD-3077M16 and wherein said second nucleic acid probe comprises a nucleic acid molecule comprising at least 10 Kb of the TBL1XR1 nucleotide sequence that is present in bacterial artificial chromosome CTD-2316F21.

2. The composition of claim 1, wherein said first nucleic acid probe comprises a nucleic acid molecule comprising at least 20 Kb of the TP63 nucleotide sequence that is present in bacterial artificial chromosome CTD-3077M16.

3. The composition of claim 1, wherein said first nucleic acid probe comprises a nucleic acid molecule comprising at least 50 Kb of the TP63 nucleotide sequence that is present in bacterial artificial chromosome CTD-3077M16.

4. The composition of claim 1, wherein said second nucleic acid probe comprises a nucleic acid molecule comprising at least 20 Kb of the TBL1XR1 nucleotide sequence that is present in bacterial artificial chromosome CTD-2316F21.

5. The composition of claim 1, wherein said second nucleic acid probe comprises a nucleic acid molecule comprising at least 50 Kb of the TBL1XR1 nucleotide sequence that is present in bacterial artificial chromosome CTD-2316F21.

* * * * *

```
                           SEQUENCE LISTING

<160> NUMBER OF SEQ ID NOS: 11

<210> SEQ ID NO 1
<211> LENGTH: 20
<212> TYPE: DNA
<213> ORGANISM: homo sapiens

<400> SEQUENCE: 1
cagtggctct acacagttag                                              20

<210> SEQ ID NO 2
<211> LENGTH: 16
<212> TYPE: DNA
<213> ORGANISM: homo sapiens

<400> SEQUENCE: 2
tgggtagtcg gtgttg                                                  16

<210> SEQ ID NO 3
<211> LENGTH: 20
<212> TYPE: DNA
<213> ORGANISM: homo sapiens

<400> SEQUENCE: 3
agaaggaggg caagatgttc                                              20

<210> SEQ ID NO 4
<211> LENGTH: 20
<212> TYPE: DNA
<213> ORGANISM: homo sapiens

<400> SEQUENCE: 4
ttctgaatct gctggtccat                                              20

<210> SEQ ID NO 5
<211> LENGTH: 100
<212> TYPE: DNA
<213> ORGANISM: homo sapiens

<400> SEQUENCE: 5
taaaaaaaca tctaaactac aagatattcc taacaacgta gaaatcctgg ggcttctctt   60
gccttatgac tattccaaca tttttatatt ctcatatatg                       100

<210> SEQ ID NO 6
<211> LENGTH: 36
<212> TYPE: DNA
<213> ORGANISM: homo sapiens

<400> SEQUENCE: 6
```
acatctctag attggaatgt gagtatcact atatcc        36

<210> SEQ ID NO 7
<211> LENGTH: 36
<212> TYPE: DNA
<213> ORGANISM: homo sapiens

<400> SEQUENCE: 7
acatctctag attggaatcc acagtacacg aacctg        36

<210> SEQ ID NO 8
<211> LENGTH: 36
<212> TYPE: DNA
<213> ORGANISM: homo sapiens

<400> SEQUENCE: 8
ttctgggtgt ccttgcagcc acagtacacg aacctg        36

<210> SEQ ID NO 9
<211> LENGTH: 1047
<212> TYPE: DNA
<213> ORGANISM: homo sapiens
<220> FEATURE:
<221> NAME/KEY: misc_feature
<222> LOCATION: 2, 3, 4, 5, 6, 7, 8, 9, 10, 11, 13, 14, 16, 17, 18, 24,
      25, 27, 31, 32, 832, 927, 935, 1041
<223> OTHER INFORMATION: n = A,T,C or G

<400> SEQUENCE: 9
cnnnnnnnnn ncnnannntt ctcnngnctc nncaactaag aatgaaggta gagtggtgga        60
ctgggaagaa catcaaattc atagtcttac aatgatttat tagaagtaaa aaagaaaaac       120
tttaaaatat gattagaagg ttttatatgg ccattcctct aaatccttta ctgtctaaaa       180
cgaagtgtgt gtgtatgatc caaacaatat cattgtttcg aatgatcaga ttcttaaata       240
cttgaatgtt cctttctatt attaatccct tcccactatg aaatatttgc caataaaaag       300
atcaacaagg aaaagagcca gaaaagagca caggctgact ttatagttaa tgaagtaagt       360
acaactgcct actttaccag gaggaaaagt ccatataaat ttctctcaac ttatattaaa       420
cgcttatcta tttgaatatt tcttttctct attttattgt acccagttta tactaatatt       480
tttgcttgtg aataggtaat aaaaatgatt actgcacgtg atgcatctat gtaaatgatt       540
agtggaataa gtattaaagc ataagatatc aattggcttt tgttttaaaa atacatttac       600
ataaatacgt accaacattc atgtagaatc tggccttggt acgaagattt agtggagatg       660
aaatgcaccc tgatggttat catctgattc attaaaatac tctctttact gctgagtatt       720
tgtaattcag ttagatttat ttcttgacat catcctacac ccccacccccc cactcaggga       780 cccaatttcc tctattttgc ttgaaaggtt gtaagtggcc aagataacta tnagtgaaaa       840
ttgtgatttc ttctaaaatt tagaagacac aaagtttaga agagaattgg aagccagaag       900
agattagaac atacatttca gaaacangtt tgcantacgt tcacgacttc ggatttgcct       960
ccctttactt ctacttttgc atccataaat ttatgcactt aaaggatgac gtggtcattg      1020
gctgatatat aagacccata ngtttac      1047

<210> SEQ ID NO 10
<211> LENGTH: 465
<212> TYPE: DNA
<213> ORGANISM: homo sapiens

<400> SEQUENCE: 10

```
ttctcttctg tacctgggat ttaaacatga aatactagaa agtgctttga gtaccttaac        60
cataaaaagt gcagaatcta aattctgtct accattttat cttttacttg aacatgtata       120
caaataaaaa attaaatcta gaatacaact gtaagattta cgacagaact cgtctccctt       180
tctatgccta tgagacttac ccatttttca gaacttagct ggtcacccta aaatgggtga       240
gatctaatat cttgctttgg aacttagcct cagactaaaa attgatttgt tgaactaatt       300
cagtggcctt cagtagcttc ctcaaatgct aattcttatc acctatctga ggcaggagag       360
gaaggtaaac acttaattca tgcaatatta gaactttaaa agttactcag tgtgttctgt       420
tgatcatcct tcaacttaat ggtagctgat accaaaaaga tctca                       465

<210> SEQ ID NO 11
<211> LENGTH: 108
<212> TYPE: DNA
<213> ORGANISM: homo sapiens

<400> SEQUENCE: 11
agaaggaggg caagatgttc caagcaacaa ggatgtcaca tctctagatt ggaatccaca        60
gtacacgaac ctggggctcc tgaacagcat ggaccagcag attcagaa                    108
```